United States Patent [19]
Ito et al.

[11] Patent Number: 5,323,770
[45] Date of Patent: Jun. 28, 1994

[54] MOUTH CAVITY SANITARY DEVICE

[75] Inventors: Kazumasa Ito, Tajimi; Toshio Makino, Ena; Masaki Ohbayashi, Tajimi; Shoji Koike, Nagoya; Jun-ichi Yoshida, Ena, all of Japan

[73] Assignee: Ricoh Elemex Corporation, Aichi, Japan

[21] Appl. No.: 753,643

[22] Filed: Aug. 30, 1991

Related U.S. Application Data

[62] Division of Ser. No. 538,277, Jun. 13, 1990, abandoned.

[30] Foreign Application Priority Data

| Jun. 23, 1989 | [JP] | Japan | 1-73685[U] |
| Jun. 26, 1989 | [JP] | Japan | 1-74682[U] |
| Jun. 26, 1989 | [JP] | Japan | 1-74683[U] |
| Jun. 26, 1989 | [JP] | Japan | 1-74684[U] |
| Jun. 26, 1989 | [JP] | Japan | 1-74685[U] |
| Jun. 30, 1989 | [JP] | Japan | 1-77099[U] |
| Dec. 20, 1989 | [JP] | Japan | 1-146909[U] |
| Dec. 21, 1989 | [JP] | Japan | 1-147494[U] |
| Dec. 21, 1989 | [JP] | Japan | 1-147495[U] |
| Dec. 21, 1989 | [JP] | Japan | 1-147496[U] |
| Dec. 21, 1989 | [JP] | Japan | 1-147497[U] |

[51] Int. Cl.⁵ .............................................. A61G 17/02
[52] U.S. Cl. ................................................... 601/162
[58] Field of Search ................... 433/80; 128/62 A, 66

[56] References Cited

U.S. PATENT DOCUMENTS

| 3,703,170 | 11/1972 | Rickman, Jr. | 128/66 |
| 3,771,517 | 11/1973 | Radecki | 128/66 |
| 4,248,589 | 2/1981 | Lewis | 433/80 |
| 4,531,913 | 7/1985 | Taguchi | 433/80 |
| 4,672,953 | 6/1987 | DiVito | 433/80 |

FOREIGN PATENT DOCUMENTS 2221240 11/1973 Fed. Rep. of Germany ... 128/62 A

*Primary Examiner*—John J. Wilson
*Attorney, Agent, or Firm*—Koda and Androlia

[57] ABSTRACT

A mouth cavity sanitary device comprising: an outer case formed in a cylindrical shape so as to be capable of being held by one hand; an elongated drive unit detachably accommodated in the outer case from a lower portion, the drive unit having a pump thereof disposed in a lower portion of the outer case; a battery detachably accommodated in the outer case from also the lower portion so as to run parallel to the drive unit, the battery being electrically connected to the motor of the drive unit; a reservoir chamber formed from the upper portion of the outer case to the portion in which the drive unit and the battery are respectively accommodated, the reservoir chamber being connected to the suction side of the pump; and a nozzle the base portion of which is detachably fastened to the upper portion of the outer case, the nozzle being connected to the discharge side of the pump.

3 Claims, 27 Drawing Sheets

MOUTH CAVITY SANITARY DEVICE

This is a division of application Ser. No. 538,277, filed Jun. 13, 1990 now abandoned.

BACKGROUND OF THE INVENTION

1. Field of the Invention

The present invention relates to a mouth cavity sanitary device for cleaning the mouth cavity or refreshing the mouth cavity by Jetting liquid, accumulated in a reservoir thereof, to the mouth cavity through a nozzle thereof by switching on a switch thereof.

2. Prior Art

Hitherto, as shown in FIG. 1, a mouth cavity sanitary device of the type described above has been constituted in such a manner that a reservoir 2 is disposed on a body 1. Furthermore, a handle 4 having a nozzle 5 detachably fastened thereto is connected to the body 1 via a tube 3, the handle 4 which has the nozzle 5 being, for example, as shown in the drawing, stood and held by the body 1. When the mouth cavity sanitary device thus constituted is used, the handle 4 is separated from the body 1 and a cap 6 thereof is removed with the separated handle 4 held by the hand before directing the nozzle 5 to the mouth cavity. Then, a switch 7 disposed close to the hand is switched so as to operate the mouth cavity sanitary device. As a result, liquid enclosed in the reservoir 2 is urged by a pump 8 provided for the body 1 so as to be jetted out from the nozzle 5 through the tube 3. Liquid thus jetted out cleans up the mouth cavity and refreshment is given to the mouth cavity.

However, a mouth cavity sanitary device constituted as described above has been very difficult to be arranged portably and it has therefore been used in a place where a user has gone because of the following reasons:

(1) It is difficult for the portable mouth cavity sanitary device to be formed compact and is necessary for a space for accommodating a battery to be provided.

(2) The capacity of the reservoir becomes unsatisfactorily small.

(3) The manufacturing of the portable mouth cavity sanitary device becomes very difficult.

Therefore, an object of the present invention is to provide a mouth cavity sanitary device capable of overcoming the above-described problems, that is, to provide a mouth cavity sanitary device capable of being formed portable so as to be used at a place where a user has gone.

Although omitted from FIG. 1, the motor 9 for operating the pump 8 is, as shown in FIG. 2, supported by a bracket q via a vibration isolating member p made of, for example, rubber so that the transmission of the vibration of the motor 9 to the bracket q is prevented. As a result, the generation of vibrations and noise in the overall body is prevented.

However, in order to perfectly prevent the generation of the vibrations and the noise, each of other elements forming the drive portion, such as gears, cranks and the pump must, as well as, be supported via a vibration isolating member. Therefore, the structure becomes excessively complicated and the number of necessary elements becomes excessively large. As a result, the assembling of the device takes a time, the overall cost can undesirably be raised and it becomes difficult to realize a compact device.

Accordingly, another object of the present invention is to provide a vibration isolating and noise eliminating structure for a mouth cavity sanitary device capable of overcoming the above-described problems, that is, to provide a vibration isolating and noise eliminating structure which does not raise the overall cost and enables a compact mouth cavity sanitary device to be realized.

The compact and thereby portable mouth cavity sanitary device which can be used at a place where a user has gone must have improved assembling facility. For example, the discharge side of the pump and the fastening portion of the nozzle must be easily connected to each other.

Therefore, a third object of the present invention is to provide a handy mouth-cavity sanitary device arranged in such a manner that the connection between the discharge side of a pump and the fastening portion of a nozzle can be easily established and the assembling facility can thereby be improved for the purpose of reducing the overall size.

When the overall size of the conventional mouth cavity sanitary device of the type as shown in FIG. 1 is desired to be reduced, its structure must be simplified as much as possible. Therefore, a portion through which liquid is supplied into the reservoir must be constituted simply as much as possible with an excellent appearance maintained.

Accordingly, a fourth object of the present invention is to provide a compact and portable mouth cavity sanitary device arranged in such a manner that the portion through which liquid is supplied to the reservoir is structured simply with an excellent appearance maintained.

According to the conventional mouth cavity sanitary device, liquid enclosed in the reservoir is sucked and urged by the pump so as to be discharged through the nozzle. The liquid urging device of the type described above has been arranged to adjust the pressure of liquid to be discharged through the nozzle by the following means:

(1) The cross sectional area of a liquid passage arranged from the pump to the nozzle is changed.

(2) A portion of liquid in the cylinder of the pump is returned to the suction side at the time of urging liquid.

(3) A plurality of nozzles having different apertures are prepared so as to select a proper one from the plurality of nozzles.

(4) The output of the motor for operating the pump is adjusted.

However, the above-described conventional structure arises the following problems:

a. The enlargement of the load of the pump cannot be prevented, causing noise and vibrations. As a result, the durability is deteriorated.

b. The structure becomes complicated excessively.

c. The number of the elements becomes too large.

Therefore, a fifth object of the present invention is to provide a liquid urging device capable of overcoming the above-described problems experienced with the conventional device and the structure of which can be simplified so as to reduce the number of necessary elements thereof and in which the pressure of liquid, to be discharged through the nozzle, can be adjusted.

Hitherto, a nozzle is, as shown in FIG. 3, fastened to a cleaner such as the mouth cavity cleaner in such a manner that an O-ring 102 is fitted within a nozzle fastening portion 104. An end portion 84 of a nozzle 81 is inserted into a nozzle insertion portion 101 and the O-ring 102 is fitted within a groove 100 formed in the outer surface of the end portion of the nozzle 81. Furthermore, as shown in FIG. 4, the nozzle 81, having an O-ring 106 fastened to the lower surface of a nozzle flange 107 secured to the nozzle 81 and having a fastening groove 105 formed in the insertion portion of the nozzle 81, is inserted into a nozzle fastening portion 104 including an elastic fastening portion 109 made of a spring member. The O-ring 106 is brought into close contact with an O-ring fastening portion 108 of the nozzle fastening portion 104. The above-described fastening groove 105 formed in the surface of the nozzle 81 and the elastic fastening portion 109 are fastened to each other so that the nozzle 81 is secured to the nozzle fastening portion 104.

However, the above-described nozzle securing structure of the conventional cleaner shows the following problem:

Since the mouth cavity cleaner is used in such a manner that the nozzle thereof is placed in the mouth cavity, the nozzle is changed for another one whenever a person who uses the mouth cavity cleaner changes. Therefore, the nozzle fastening portion deteriorates in its sealing performance due to wear in proportion to the number of times of the changes of the nozzles.

However, according to the nozzle fixing structure shown in FIG. 3, the O-ring deteriorates excessively. Therefore, the nozzle fastening portion 104 must be decomposed so as to be repaired when the O-ring is maintained or exchanged. As a result, it takes an excessively long time to perform the after service.

Furthermore, the elastic fastening portion 109 for holding the nozzle 81 must be additionally provided for the nozzle securing structure shown in FIG. 4, causing the overall cost to be enlarged.

Therefore, a sixth object of the present invention is to provide a cleaner arranged in such a manner that the nozzle fixing structure thereof is structured simply and its O-ring can be easily maintained or exchanged.

Hitherto, a mouth cavity sanitary device of the type described above has been arranged to comprise a pump for sucking and urging liquid as shown in FIG. 5. Referring to the drawing, a pump case 121 is, for example, constituted by a first, a second and a third pump cases 122, 123 and 124. The first pump case 122 is provided with a cylinder 122a which accommodates a piston 125 in such a manner that the piston 125 can be reciprocated. The second pump case 123 is fastened to the left side of the first pump case 122 when viewed in the drawing, the second pump case 123 being fastened via a valve supporting member 127 which supports a stopper valve 126 in such a manner that the stop valve 126 can be reciprocated. The second pump case 123 is provided with an inlet port 123a and a valve seat 123b for the stop valve 126. On the other hand, the third pump case 124 is fastened to the right side of the first pump case 122 when viewed in the drawing, the third pump case 124 having a discharge port 124a formed therein. Thus, the piston 125 is reciprocated with the stop valve 126 opened/closed so that liquid sucked into the cylinder 122a through the inlet port 123a is discharged through the discharge port 124a.

However, the above-described conventional pump structure shows the following problems:

(1) If air is introduced into the pump case 121, air can be accumulated in the cylinder 122a, causing the liquid discharge pressure to become irregular or the discharge pressure to be lowered.

(2) Since the pump case 121 is constituted by the first, the second and the third pump cases 122, 123 and 124 and the valve supporting member 127 must be provided, the number of the elements becomes excessively large.

(3) If the stop valve 126 cannot return to the close position due to the compression operation performed by the piston 125, the liquid discharge pressure is excessively lowered, causing the pump function to be lost.

Accordingly, a seventh object of the present invention is to provide a pump structure for a mouth cavity sanitary device capable of overcoming the above-described problems experienced with the conventional structure and in which the accumulation of air introduced into the pump case can be prevented, the number of the necessary elements can be reduced, and the problem arises in that the stop valve cannot return to the close position due to the compression operation performed by the piston can be overcome.

SUMMARY OF THE INVENTION

In order to achieve the above-described first object of the present invention, there is, as described referring to the following embodiments, provided a mouth cavity sanitary device comprising: an outer case 10 formed in a cylindrical shape so as to be capable of being held by one hand; an elongated drive unit 15 detachably accommodated in the outer case 10 from a lower portion, the drive unit 15 having a pump 25 thereof disposed in a lower portion of the outer case 10; a battery 17 detachably accommodated in the outer case 10 from also the lower portion so as to run parallel to the drive unit 15, the battery 17 being electrically connected to the motor 20 of the drive unit 15; a reservoir chamber 34 formed from the upper portion of the outer case 10 to the portion in which the drive unit 15 and the battery 17 are respectively accommodated, the reservoir chamber 34 being connected to the suction side 25a of the pump 25; and a nozzle 37 the base portion 37a of which is detachably fastened to the upper portion of the outer case 10, the nozzle 37 being connected to the discharge side 25b of the pump 25.

The base portion 37a of the nozzle 37 is directly fastened to the upper portion of the cylindrical outer case 10 which also serves as a handle. On the other hand, the reservoir chamber 34 is formed in the upper portion of the outer case 10 and the drive unit 15 and the battery 17 are efficiently and in parallel accommodated in the outer case 10 from a lower portion.

In order to achieve the above-described second object of the present invention, the vibration isolating and noise eliminating structure according to the present invention is, as described referring to the following embodiments, realized in a mouth cavity sanitary device for cleaning the mouth cavity or the like with liquid jetted out through a nozzle 37 from a reservoir 34 by a pump 25 operated by a motor 20, the mouth cavity sanitary device comprising: a unit which is constituting by integrating the drive portions such as the motor 20, the pump 25 and the like, the drive unit 15 being secured to the inside of the outer case 10 via a vibration isolating members 50 and 52.

Thus, vibrations generated in the motor 20 or the pump 25 can be absorbed by the vibration isolating members 50 and 52 so as not to be transmitted to the outer case 10.

In order to achieve the above-described third object of the present invention, there is, as described referring to the following embodiments, provided a mouth cavity sanitary device for cleaning the mouth cavity or the like with liquid urged and Jetted out through a nozzle 37 from a reservoir chamber 34 by a pump 25 which is arranged to be operated when a switch 40 is operated, the mouth cavity sanitary device comprising: an outer case 10 formed in a cylindrical shape so as to be capable of being held by one hand; and a connection tube 38 for establishing the connection in the outer case 10 between the discharge side 25b of the pump 25 and the fastening portion 12c of the nozzle 37.

The discharge side 25b of the pump 25 and the fastening portion 12c of the nozzle 37 are connected to each other by the connection tube 38 so that liquid in the reservoir chamber 34 is urged by the pump 25 so as to be discharged through the nozzle 37.

In order to achieve the above-described fourth object of the present invention, there is, as described referring to the following embodiments, provided a mouth cavity sanitary device for cleaning the mouth cavity or the like with liquid urged and Jetted out through a nozzle 37 from a reservoir chamber 34 by a pump 25 which is arranged to be operated when a switch button 40 is operated, the mouth cavity sanitary device comprising: an outer case 10 formed in a cylindrical shape so as to be capable of being held by one hand and having the reservoir chamber 34 formed in the upper portion thereof; a nozzle fastening port 12a formed at the top end surface of the outer case 10; and a liquid supply port 12b communicated with the reservoir chamber 34 is formed in the nozzle fastening port 12a.

Liquid is supplied through the nozzle fastening port 12a after the nozzle 37 has been removed into the reservoir chamber 34 through the liquid supply port 12b. Then, the nozzle fastening port 12a is covered by fastening the nozzle 37.

In order to achieve the above-described fifth object of the present invention, there is, as described referring to the following embodiments, provided a liquid urging device for discharging liquid through a nozzle 37 by urging and sucking liquid in a reservoir chamber 34 by operating a pump 25, the liquid urging device comprising: a circulating hole 37b formed in the nozzle 37; a circulating passage constituted by, for example, a nozzle fastening port 12a and a liquid supply hole 12b, and formed in the fastening portion 12c of the nozzle 37, the circulating passage acting to return liquid flowed out through the circulating hole 37b to the reservoir chamber 34.

A shutter member 55 for adjusting the opening degree of the circulating hole 37b may be fastened to the nozzle 37.

A proper nozzle 37 having different circulating hole 37b is selected for the opening degree of the circulating hole 37b formed in the nozzle 55 is adjusted by the shutter member so that the pressure of liquid to be discharged through the nozzle 37 is adjusted.

In order to achieve the above-described sixth object of the present invention, there is, as described referring to the following embodiments, provided a nozzle securing structure for a cleaner having a pump 25, the nozzle securing structure comprising: a nozzle 37 having a liquid passage 91 formed therein and having a nozzle flange portion 96 which has an outer groove formed at the end portion of the nozzle 37 to which an O-ring 36 is fitted within the outer groove; a fastening portion 12c having a nozzle insertion port 83 the inner diameter of which is smaller than the outer diameter of the O-ring 36 and an O-ring fastening portion 87 the inner diameter of which is larger than the inner diameter of the nozzle insertion port 83 so that liquid discharged from the pump 25 is introduced into the liquid passage 91 and an inlet portion 97 of a nozzle fastening portion 12a which can be engaged to the nozzle flange portion 96 when the nozzle 37 is fastened to the fastening portion 12c.

In order to Jet out liquid discharged from the pump 25 through a nozzle discharge port 92 formed at the front end portion of the nozzle 37, an end portion 84 of the nozzle 37 is inserted into the nozzle insertion port 83 so as to secure the nozzle 37 to the fastening portion 12c. As a result, even if the performance for sealing between the fastening portion 12c and the O-ring 36 is deteriorated since the O-ring is deteriorated due to the repeated mounting/detaching of the nozzle 37 on/from the fastening portion 12c or the lapse of time, the maintenance of the O-ring 36 held by the nozzle 37 can be easily performed. According to the nozzle securing structure according to the present invention and inserted into the fastening portion 12c, since the outer surface of the O-ring 36 and the O-ring fastening portion 87 can be brought into hermetically contact with each other, the leakage of liquid outside the nozzle 37 can be prevented and liquid can be introduced into the liquid passage 91, the liquid being discharged by the urging force of the pump 25. Furthermore, the outer surface of the O-ring 36 and the O-ring fastening portion 87 can be brought into hermetically contact with each other in a state where the nozzle 37 has been fastened to the fastening portion 12c. In addition, the nozzle flange portion 96 and the inlet portion 97 of the nozzle fastening port 12a are engaged to each other. Therefore, the nozzle 37 can be secured in such a manner that the outer surface of the O-ring 36 is pressed in the direction toward the nozzle insertion port 83. As a result, the sealing performance of the sealing portion of the O-ring 36 can be improved.

In order to achieve the above-described seventh object of the present invention, there is, as described referring to the following embodiments, provided a pump structure for a mouth cavity sanitary device for discharging, through a discharge port 46b, liquid sucked into its cylinder 46a through a suction port 47b with opening/closing a stopper valve 48 by reciprocating a piston 26, the mouth cavity sanitary device comprising: a structure arranged in such a manner that the pump structure is arranged such that the discharge port 46b is disposed upper than the suction port 47b. Thus, air introduced into a pump case 45 is discharged through the discharge port 46b. The pump case 45 is constituted by a first and a second pump cases 46 and 47, the cylinder 46a, the discharge port 46b and a valve supporting portion 46c are provided for the first pump case 46 and a valve seat 47a for the stop valve 48 and the suction port 47b are provided for the second pump case 47. Furthermore, the conventional valve supporting member or the third pump case are eliminated. Furthermore, the direction of operation of the piston 26 and that of the stop valve 48 are made the same and a valve rod 49 is pushed so as to push the stop valve 48 toward a valve seat 47a when the stop valve 48 does not return to the close position due to the compression operation of the piston 26.

Other and further objects, features and advantages of the invention will appear more fully from the following description.

PREFERRED EMBODIMENTS OF THE PRESENT INVENTION

Preferred embodiments of the present invention will now be described with reference to the drawings.

Figure 1:
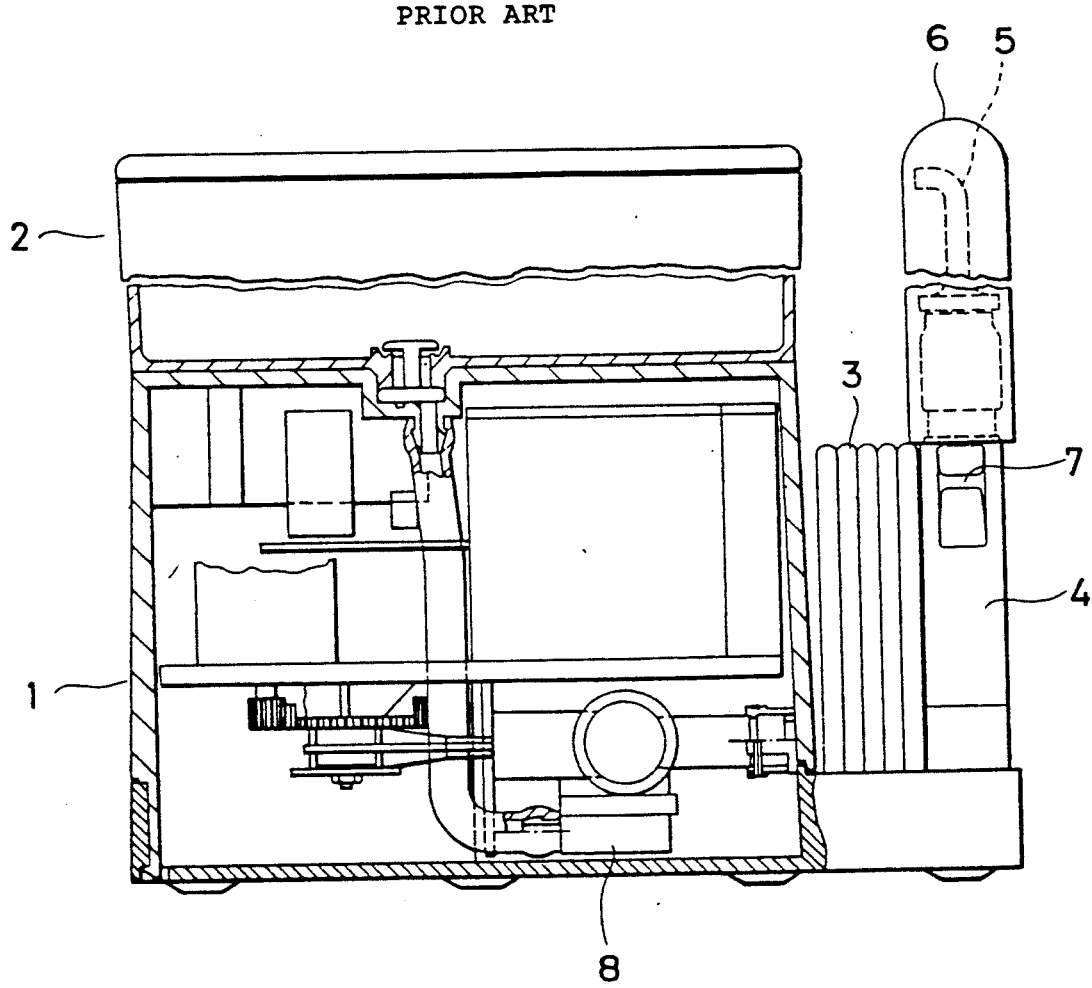
FIG. 1 is a schematic view which illustrates a conventional mouth cavity sanitary device.
Figure 2:
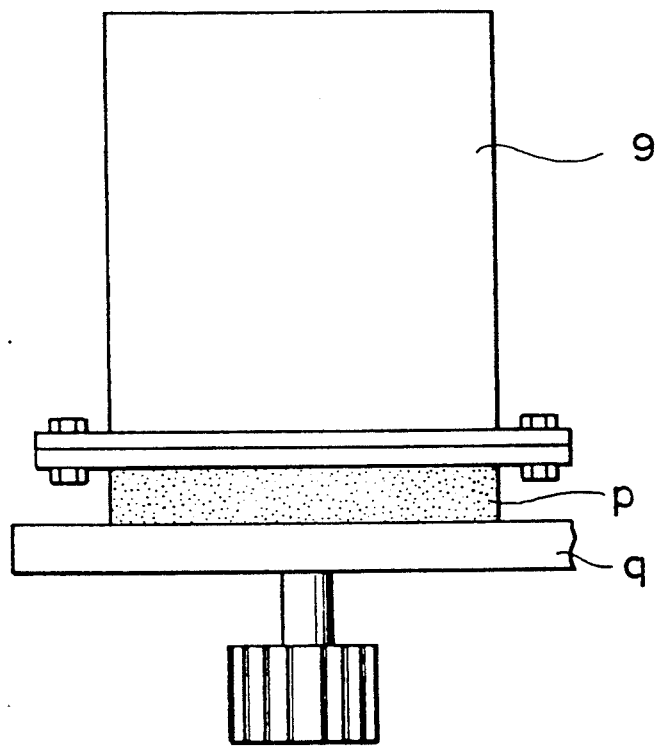
FIG. 2 illustrates a motor supporting structure for the conventional mouth cavity sanitary device shown in FIG. 1.
Figure 3:
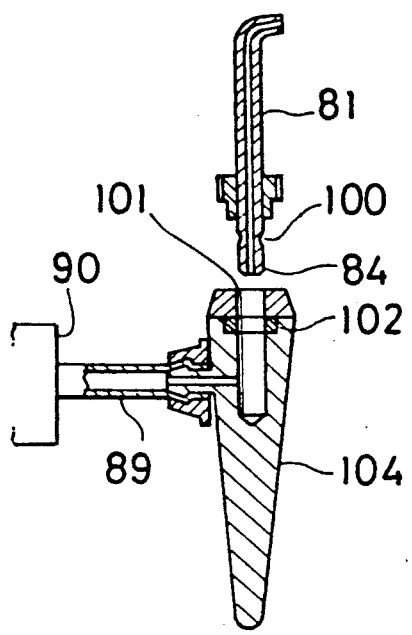
FIG. 3 is a cross sectional view which illustrates a nozzle securing structure for the conventional mouth cavity sanitary device.
Figure 4:
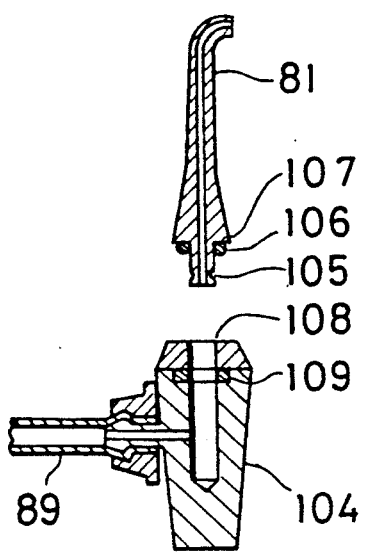
FIG. 4 is a cross sectional view which illustrates another nozzle-securing structure for the conventional mouth cavity sanitary device.
Figure 5:
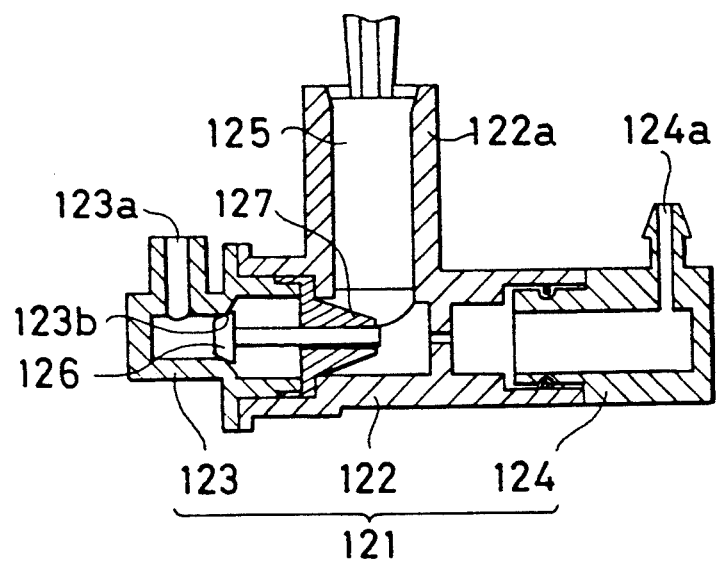
FIG. 5 is a cross sectional view which illustrates a conventional pump structure for the mouth cavity sanitary device.
Figure 6:
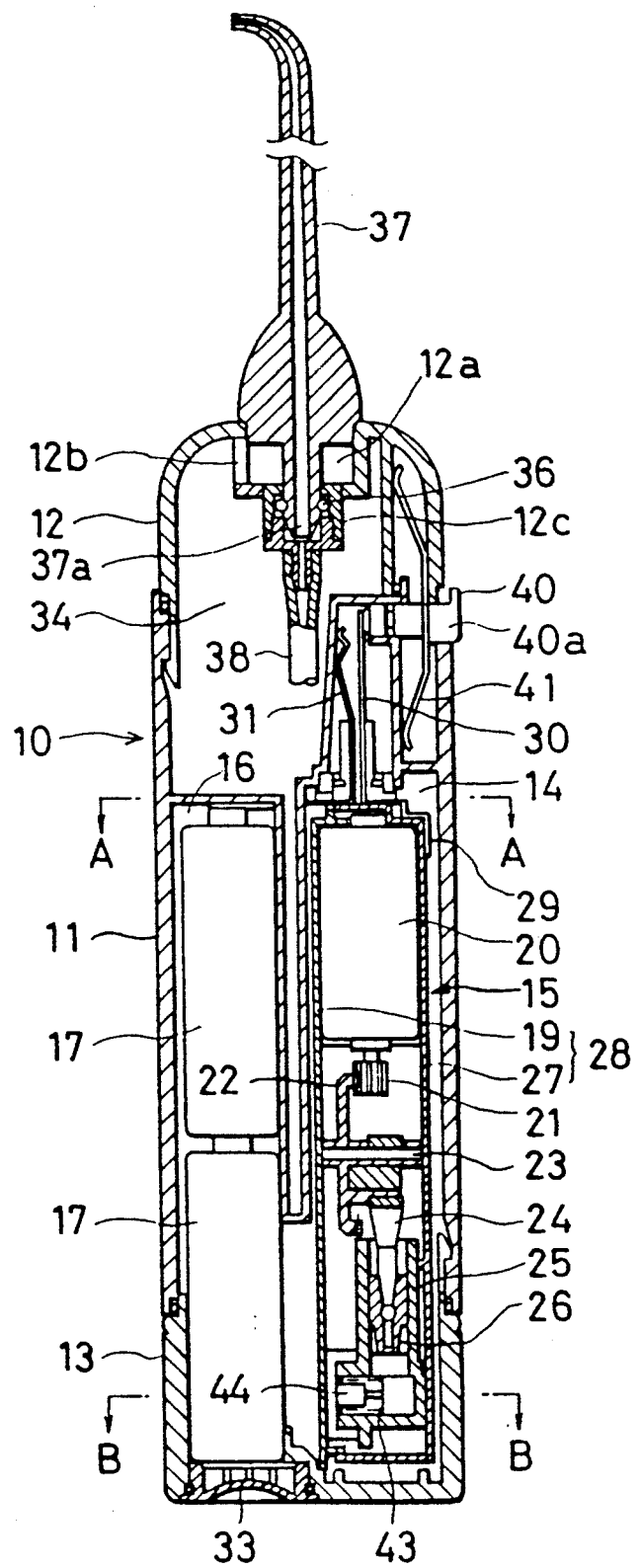
FIG. 6 is an overall cross sectional view which illustrates an embodiment of the mouth cavity sanitary device according to the present invention.

FIG. 6 illustrates an embodiment of a mouth cavity sanitary device according to the present invention. Referring to the drawing, reference numeral 10 represents a cylindrical outer case which can be held by one hand, the outer case 10 being constituted by an upper case 12 fastened on to a body case 11 and a lower case 12 fastened under the body case 12. A unit accommodating portion 14 is formed in a portion inside the side surface in a region from the body case 11 to the lower case 13. In the unit accommodating portion 14, an elongated drive unit 15 is detachably accommodated. On the other hand, a battery accommodating portion 16 is formed in a portion inside another side surface in a region from the body case 11 to the lower case 13. In the battery accommodating portion 16, two batteries 17 are detachably accommodated.

Figure 7:
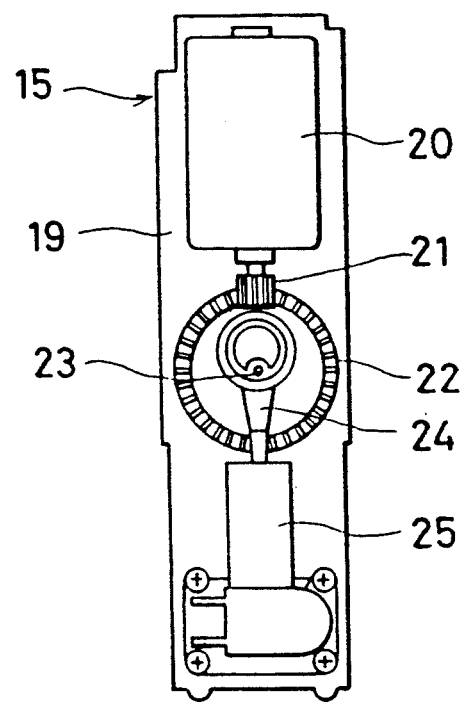
FIG. 7 is an internal structure view which illustrates a drive unit for use in the mouth cavity sanitary device according to the embodiment of the present invention.

Also as shown in FIG. 7, the drive unit 15 is arranged in such a manner that a motor 20 is fastened to a plate-like substrate 19. A crown gear 22 is engaged to a motor gear 21 of the motor 20 so as to be rotatably supported by a secured shaft 23 erected on the substrate 19. An end portion of a crank 24 is eccentrically and rotatably fastened to the crown gear 22. On the other hand, a piston 26 of a pump 25 is fastened to another end portion of the crank 24. The pump 25 is fastened to the surface of the substrate 19. A semi-cylindrical cap 27 is fitted on the substrate 19 so that a unit case 28 is constituted by the substrate 19 and the cap 27. In the thus constituted unit case 28, a drive portion comprising the above-described motor 20, the crown gear 22 and the pump 25 is accommodated. A positive terminal plate 29 and a negative terminal plate (omitted from illustration) are disposed on the outer surface of the unit case 28. Two switch springs 30 and 31 running parallel to each other are extended from the positive terminal plate 29. The drive unit 15 is, from the lower portion, detachably inserted into the unit accommodating portion 14 of the body case 11. Then, as shown in FIG. 6, the switch springs 30 and 31 are, with made to face upwards, stretched and the pump 25 is positioned in the lower portion so as to be accommodated in the outer case 10.

On the other hand, the batteries 17 are inserted, from the lower portion, into the battery accommodating portion 16 of the body case 11 after a battery cover 33 of the lower case 13 shown in FIG. 6 has been removed. Then, two batteries 17 are in series accommodated in the outer case 10 with disposed in parallel to the drive unit 15. Then, the positive side of the battery 17 is connected to a front portion 29a of the positive terminal plate 29 shown in FIG. 8, while the negative side of it is connected to the negative terminal plate (omitted from illustration) so that the two batteries 17 are electrically connected to the motor 20 of the drive unit 15.

Figure 8:
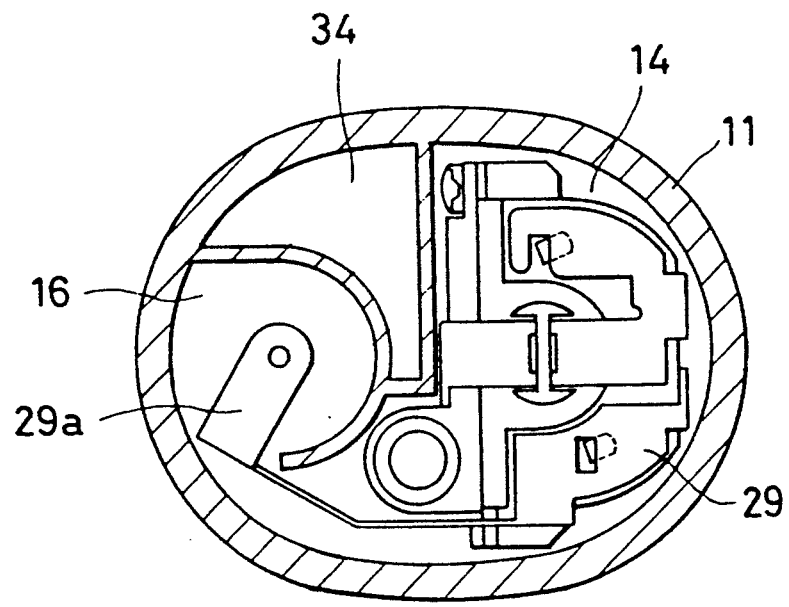
FIG. 8 is a lateral cross sectional view taken along line A—A of FIG. 6.
Figure 9:
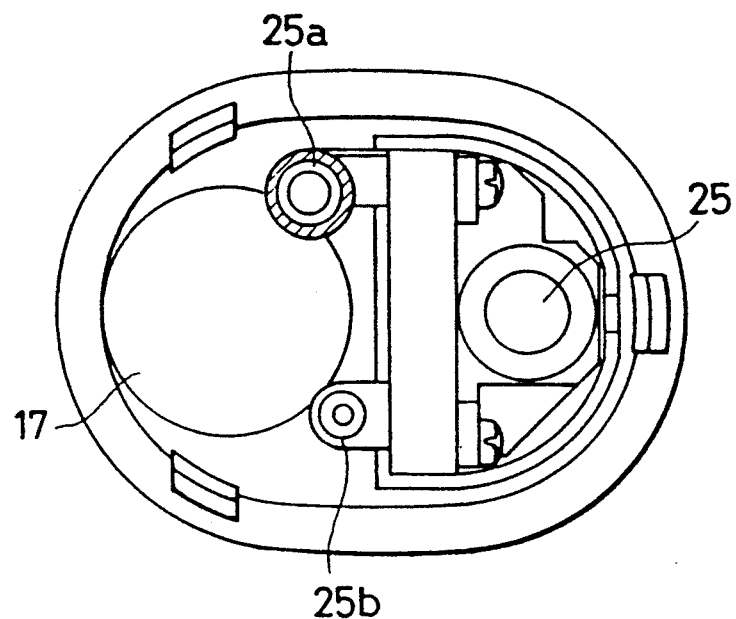
FIG. 9 is a lateral cross sectional view taken along line B—B of FIG. 6.
Figure 10:
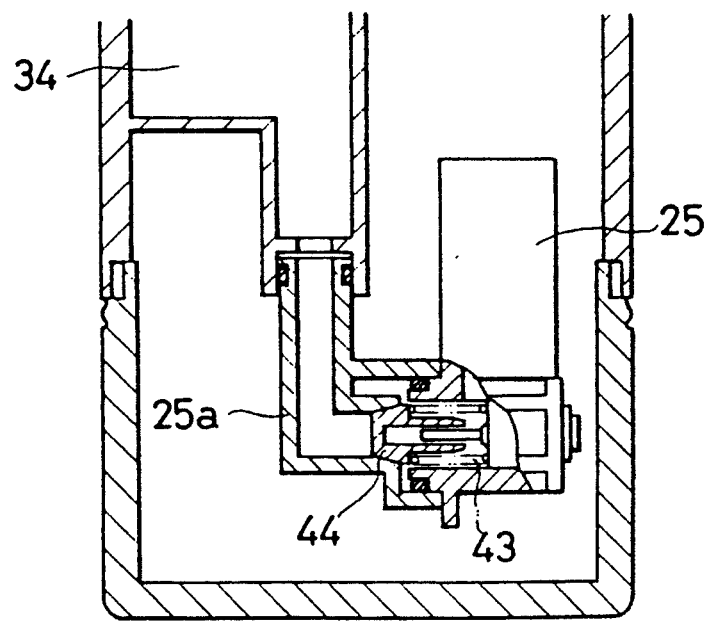
FIG. 10 is a cross sectional view which illustrates a suction side of the pump.

As can be seen from FIG. 6, the outer case 10 includes a reservoir chamber 34 formed in a region from the upper portion thereof to the portion for accommodating the drive unit 15 and the batteries 17. That is, the reservoir chamber 34 is disposed on the inside of the upper case, that is, on the body case 11. As shown in FIG. 8, the reservoir chamber 34 is disposed between the unit accommodating portion 14 and the battery accommodating portion 16. The reservoir chamber 34 is, as shown in FIGS. 9 and 10, connected to the suction side 25a of the pump 25.

Figure 12:
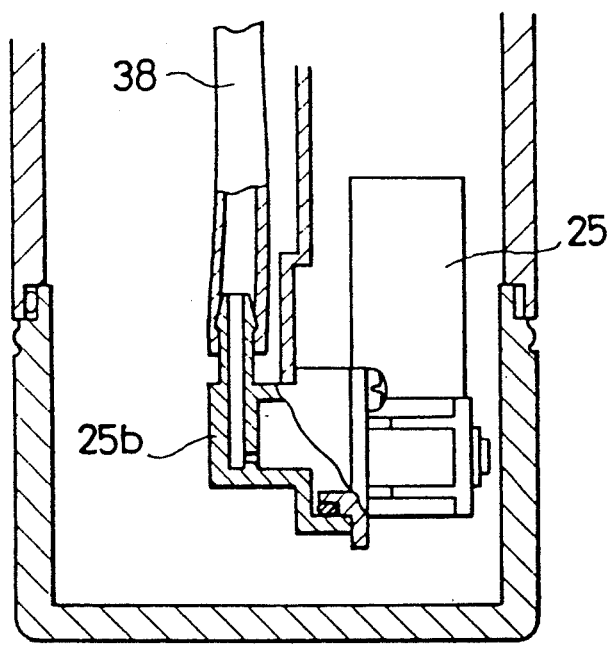
FIG. 12 is a partial enlarged cross sectional view which illustrates the discharge portion shown in FIG. 11.
Figure 18:
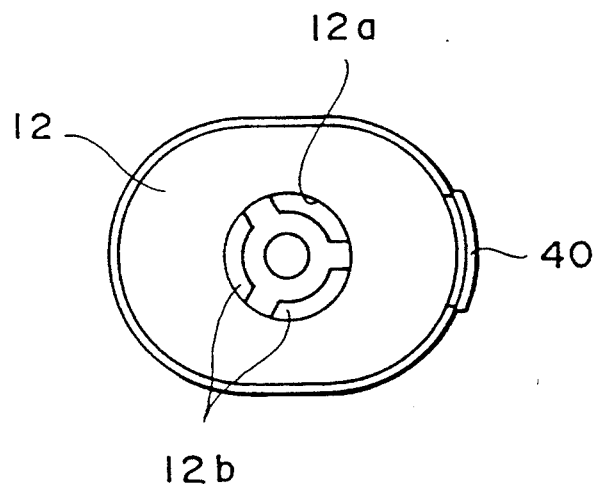
FIG. 18 is a plan view which illustrates the mouth cavity sanitary device in a state where the nozzle has been removed therefrom.

As shown in FIGS. 6 and 18, the mouth cavity sanitary device is further arranged to have a recessed portion formed in the upper portion of the outer case 10, that is, in the top surface of the upper case 12. A nozzle fastening port 12a is formed in the recessed portion. The nozzle fastening port 12a has a liquid supply port 12b formed therein, the liquid supply port 12b being connected to the reservoir chamber 34. Furthermore, a fastening portion 12c having an O-ring 36 is also provided for the nozzle fastening port 12a. A base portion 37a is fitted to the fastening portion 12c and a nozzle 37 is detachably fastened to the nozzle fastening port 12a. As a result, the liquid leakage from a gap formed between the base portion 37a and the fastening portion 12c can be prevented by the O-ring 36. An end portion of a connection tube 38 is connected to the fastening portion 12. Another end portion of the connection tube 38 passes through the reservoir chamber 34 and extends downwards to a discharge side 25b of the pump 25 at which the connection tube 38 is, as shown in FIG. 12, connected to the same. The discharge side 25b is, as shown in FIG. 9, disposed away from the above-described inlet side 25a.

As shown in FIG. 6, a switch button 40 is fastened in the upper portion of the body case 11, the switch button 40 being arranged in such a manner that the front end portion thereof is positioned so as to confront the front portion of either of switch button springs 30 and is outwards urged by a return spring 41 so that a head portion 40a of the switch button 40 projects over the outer surface of the body case 11. As a result, when the switch button 40 is depressed against the urging force of the return spring 41, the two switch button springs 30 and 31 can be brought into contact with each other so that the motor 20 is operated.

When the thus constituted mouth cavity sanitary device is used, water or chemical (for example, mouth cavity cleaning liquid or liquid obtained by diluting it) is introduced through the nozzle fastening port 12a of the upper case 12 and the liquid supply port 12b into the reservoir chamber 34. After the reservoir chamber 34 has been filled with liquid thus introduced, the base portion 37a is fitted to the fastening portion 12c before capping the nozzle fastening port 12a with the nozzle 37. Then, the outer case 10 is held by a user who has become slouchy and the nozzle 37 is directed at the mouth cavity before depressing the switch button 40. As a result, the motor 20 is operated so that the motor gear 21 is rotated, causing the crown ger 22 to be rotated. Therefore, the piston 26 is reciprocated via the crank 24 so that the stop valve 44 (see FIGS. 6 and 10) is opened against the urging force of the urging spring 43 in the suction stroke, causing liquid enclosed in the reservoir chamber 34 to be introduced. In the discharge stroke, the stop valve 44 is closed so as to upwards send the thus introduced liquid through the connection tube 38. Then, liquid is jetted out through the nozzle so as to be discharged in the mouth cavity. As a result, the mouth cavity can be cleaned up and the mouth cavity can be refreshed. When the hand is released from the switch button 40, the switch button 40 can be automatically returned by an action of the return spring 41. As a result, the contact between the two switch springs 30 and 31 is released so as to stop the rotation of the motor 20. Therefore, the operation of the pump 25 is stopped and the Jetting out of liquid through the nozzle 37 is stopped.

Therefore, the following effects can be obtained according to the present invention:

(1) According to the present invention, the nozzle is directly fastened to the upper portion of the cylindrical outer case and batteries which are, in series to the elongated drive unit, disposed so as to run parallel to each other are compactly accommodated in the outer case. Furthermore, the reservoir chamber is efficiently disposed. As a result, the overall size can be reduced and space for accommodating the batteries can be secured.

(2) Since the pump is disposed in the lower portion of the outer case and the reservoir chamber is formed between the drive unit and the batteries, a relatively large capacity reservoir chamber can be secured by utilizing the dead space in the cylindrical outer case.

(3) Since the drive portion is arranged to be one unit and inserted, together with the batteries and in parallel to the batteries, into the cylindrical outer case from the lower portion so as to be accommodated in the outer case, the elements can be easily assembled.

(4) Since the outer case is arranged cylindrical which can be fitted to the hand and the drive unit and the batteries are disposed so as to run parallel to each other, an excellent weight balanced state can be realized, causing the handling facility to be improved.

(5) Since the pump is disposed in the lower portion of the outer case, liquid enclosed in the reservoir chamber can be completely consumed.

Figure 13:
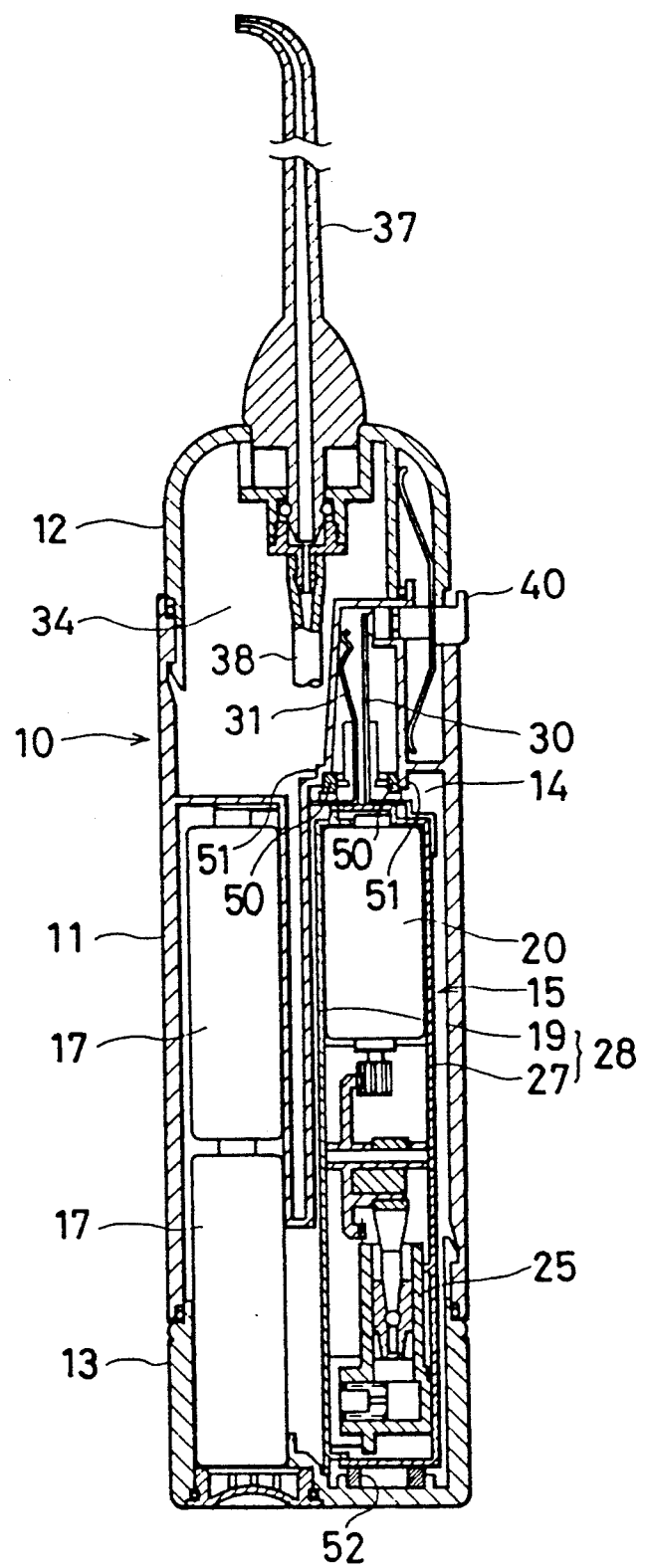
FIG. 13 is an overall vertical cross sectional view which illustrates the mouth cavity sanitary device having a vibration isolating member according to an embodiment of the present invention.

FIG. 13 is a cross sectional view which illustrates an embodiment of a vibration isolating and noise eliminating structure for the mouth cavity sanitary device according to the present invention.

Figure 14:
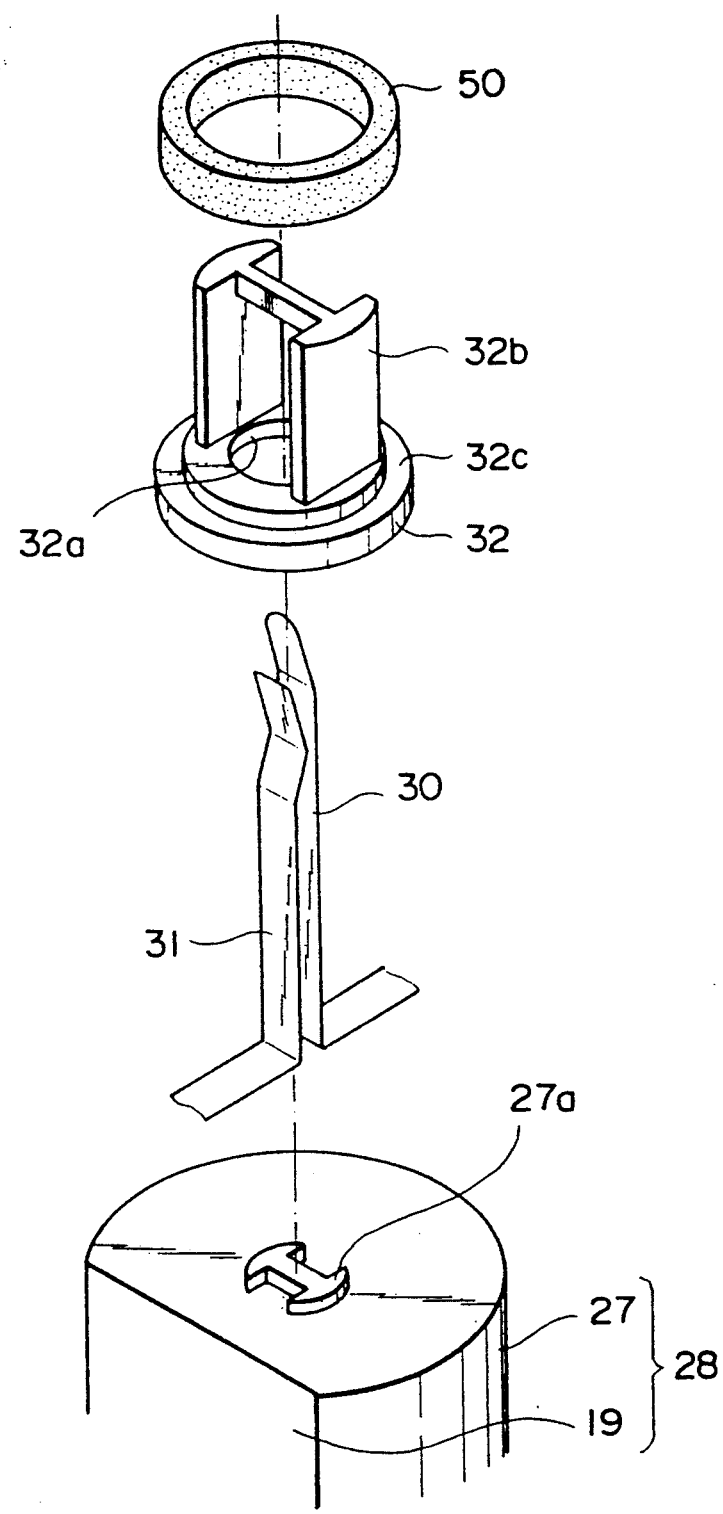
FIG. 14 is a partial exploded perspective view which illustrates a drive unit for the mouth cavity sanitary device shown in FIG. 13.
Figure 15:
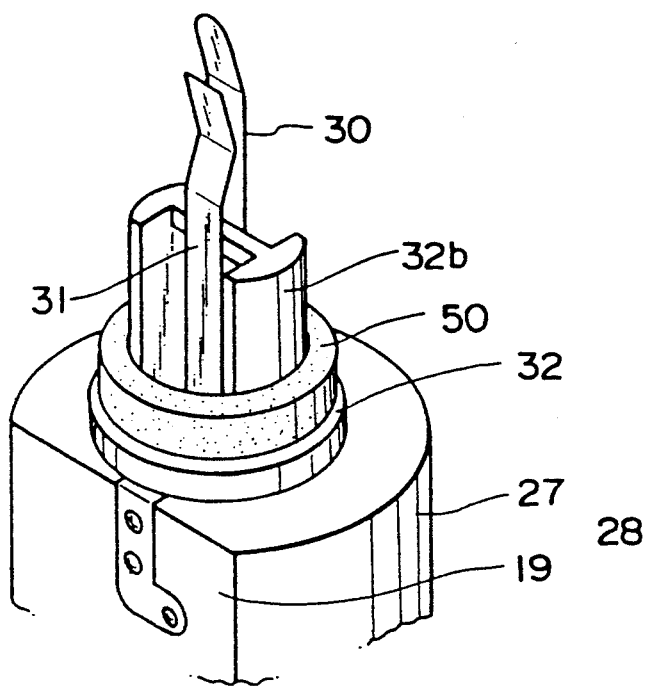
FIG. 15 is a perspective view which illustrates the assembled state of the same.
Figure 16:
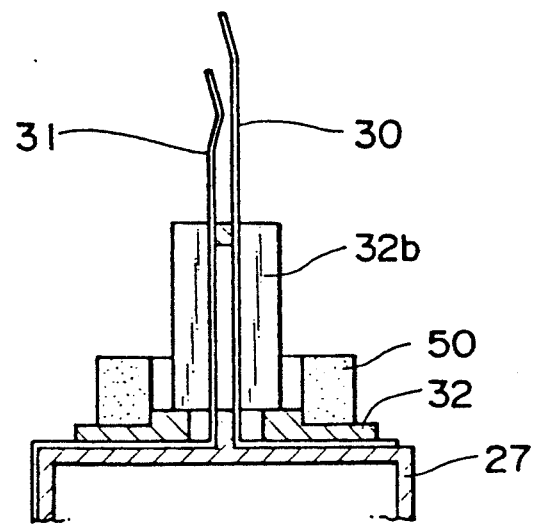
FIG. 16 is a vertical cross sectional view which illustrates the drive unit for the mouth cavity sanitary device shown in FIG. 13.

As shown in FIG. 14, the lower portions of the switch springs 30 and 31 are positioned by an H-shaped projection 27a of the cap 27 and are separated from each other. Then, the switch springs 30 and 31 are upwards stretched so as to be passed through a center hole 32a of a holder 32 before fastening the holder 32 to the cap 27. Then, the upper portions of the two switch springs 30 and 31 are positioned by an H-shaped column 32b of the holder 32 and are separated from each other. An annular vibration-isolating member 50 is fitted at an outer stepped portion 32c of the holder 32. FIGS. 15 and 16 illustrate a state in which the assembling has been completed. Then, the lower case 13 is removed and the drive unit 15 is inserted from the lower portion into the unit accommodating portion 14 of the body case 11 in such a manner that the drive unit 15 is disposed detachably. As shown in FIG. 13, the vibration isolating member 50 is abutted against a frame 51 in the outer case 10 and is positioned there before capping the lower case 13. Then, another vibration isolating member 52 is sandwiched by the lower case 13, and the switch springs 30 and 31 are upwards stretched. Then, the drive unit 15 is assuredly secured into the outer case 10 with the pump 25 disposed in the lower portion of the outer case 10.

Therefore, according to the present invention, the overall body of the drive portion is arranged to be one unit and the drive unit thus arranged is secured in the outer case via the vibration isolating members. Therefore, the necessity of providing a vibration isolating member to each of the vibrating members, causing the number of the necessary elements to be reduced. Therefore, the overall cost can be reduced and the vibration and noise can be prevented without a necessity of enlarging the overall size of the device. Furthermore, since the drive portion is arranged to be one unit, the handling can be facilitated and the assembling of the elements can be easily performed.

Figure 11:
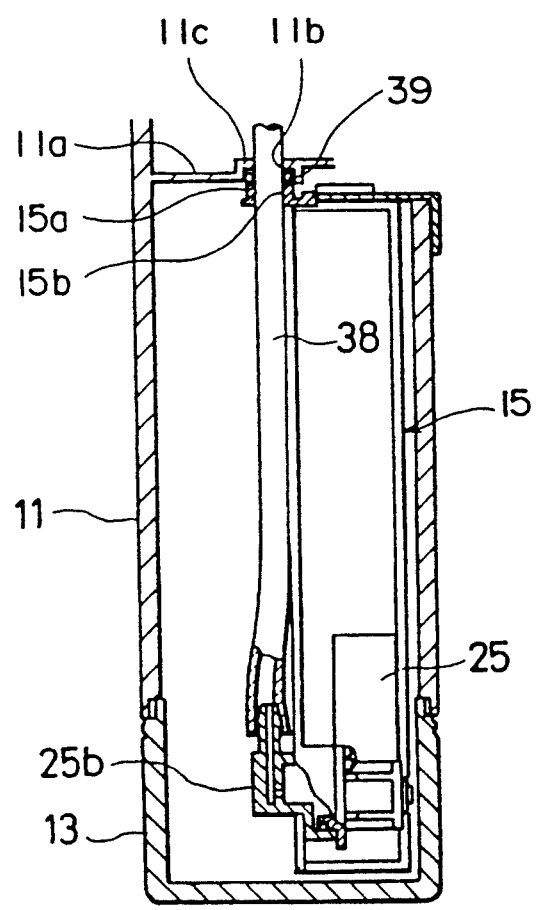
FIG. 11 is a cross sectional view which illustrates a discharge side of the same.

As described referring to FIG. 6, the base portion 37a of the nozzle 37 is fitted to the fastening portion 12c having the O-ring 36 and the nozzle 37 is detachably fastened to the nozzle fastening port 12a. Therefore, the liquid leakage from the gap between the base portion 37a and the fastening portion 12c can be prevented by the O-ring 36. An end portion of the connection tube 38 is connected to the fastening portion 12c. The connection tube 38 is arranged so as to vertically pass through the reservoir chamber 34 and another end portion thereof is, as shown in FIG. 11, inserted into a tube hole 11b formed in the bottom wall 11a before stretched downwards. An O-ring 39 is fastened to the outer surface of the connection tube 38, the O-ring being then placed in a recessed portion 11c. Thus, the connection tube 38 is inserted into a tube hole 15b of a retaining portion 15a, the drive unit 15 is inserted into the body case 11 and the O-ring 39 placed in the recessed portion 11c is pressed by the retaining portion 15a. As a result, the downward leakage of liquid in the reservoir chamber 34 through the tube hole 11b can be prevented. Then, the other end portion of the connection tube 38 is, as shown in FIG. 12, connected to the discharge side 25b of the pump 25. The discharge side 25b is, as shown in FIG. 9, positioned away from the abovedescribed suction side 25a.

As a result, the following effects can be obtained:

(1) Even if there is a positional deviation between the discharge side of the pump and the fastening portion of the nozzle, these two elements can be easily connected.

(2) Since it is simply necessary to connect the tube, the assembling work can be easily completed.

(3) Since the assembling work can be easily completed, the structure can be applied to a mouth cavity sanitary device the overall size of which has been reduced by being accommodated in a cylindrical outer case. Therefore, a portable mouth-cavity sanitary device can be realized.

Figure 17:
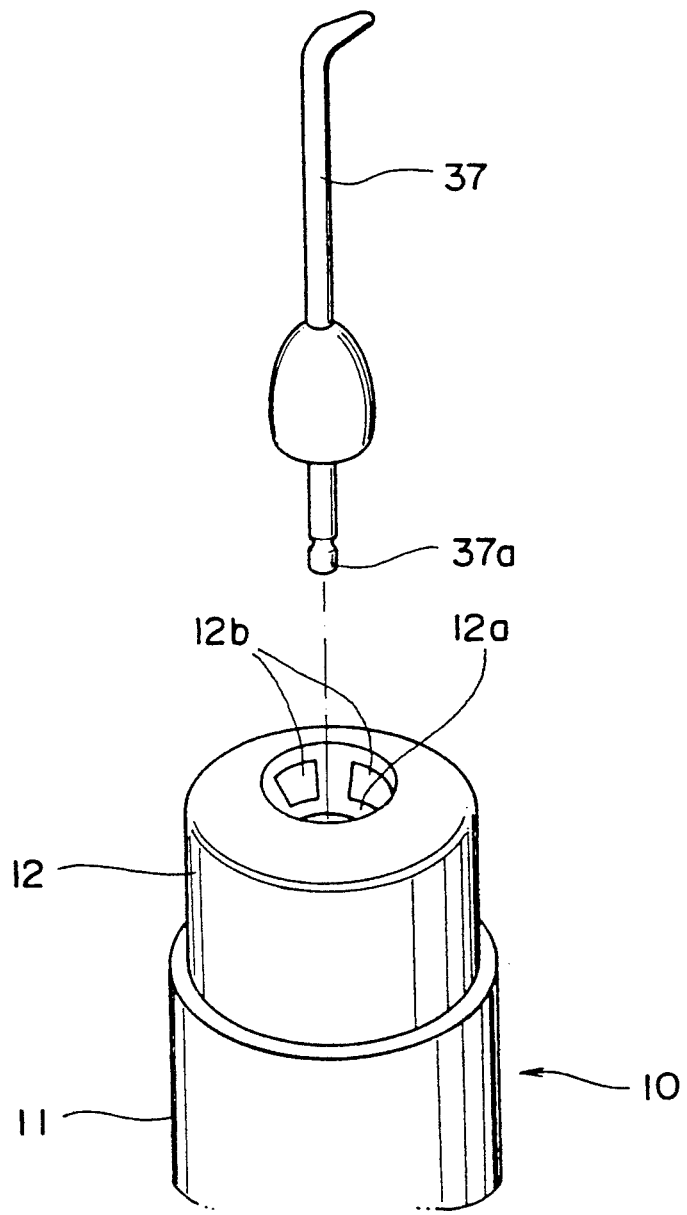
FIG. 17 is a partial perspective view which illustrates the appearance of a nozzle fastening portion and a liquid supply port of the mouth cavity sanitary device according to the present invention.

FIG. 17 is a perspective view which illustrates the nozzle fastening port and the liquid supply port formed in the nozzle fastening port of the mouth cavity sanitary device according to the present invention.

As is shown from FIGS. 6 and 17, according to the present invention, the nozzle fastening port 12a is covered with the nozzle 37 so as to prevent the leakage of liquid in the reservoir chamber 34 through the nozzle fastening port 12a even if the mouth cavity sanitary device is inclined to a certain degree. However, the structure must be arranged in such a manner that the nozzle fastening port 12a is not completely closed by the nozzle 37 and air can be introduced into the reservoir chamber 34 through a gap formed between the nozzle 37 and the nozzle fastening port 12a in accordance with the reduction in the quantity of liquid.

Therefore, according to the present invention, the nozzle fastening port is formed at the top portion of the outer case and the liquid supply port communicating with the reservoir chamber is formed in the nozzle fastening port. Furthermore, liquid is supplied into the reservoir chamber through the thus formed liquid supply port. Therefore, the following effects can be obtained.

(1) Since the nozzle fastening port and the liquid supply port are positioned in the same place, the liquid supply port can be formed without complicating the structure.

(2) Since the nozzle fastening port and the liquid supply port can be positioned in the same place, the overall size can be reduced.

(3) Since the nozzle thus fastened can cover the liquid supply port, an excellent appearance can be realized, (4) Since the liquid supply port can be covered during the nozzle fastening action, liquid leakage can be prevented.

Figure 19:
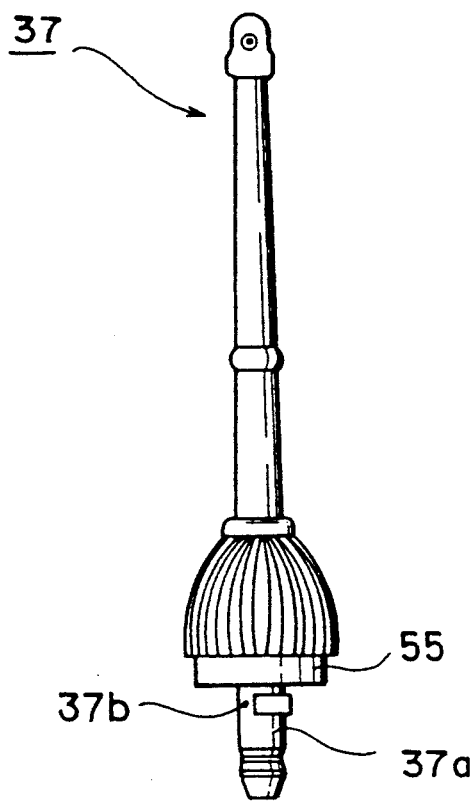
FIG. 19 is a front elevational view which illustrates the nozzle for the mouth cavity sanitary device according to the present invention.
Figure 20:
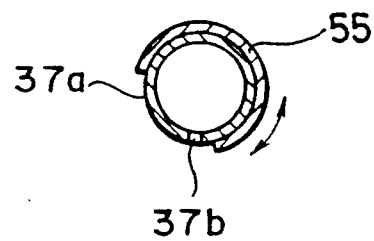
FIG. 20 is a lateral cross sectional view which illustrates a circulation hole portion of the nozzle for the mouth cavity sanitary device according to the present invention.
Figure 22:
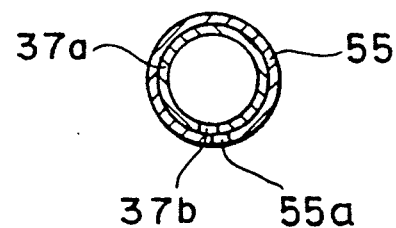
FIG. 22 is a lateral cross sectional view which illustrates another example of a shutter portion of the circulation hole portion shown in FIG. 20.
Figure 21:
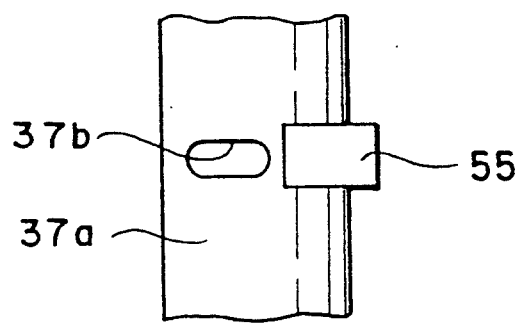
FIG. 21 illustrates another structure of the circulation hole portion of the nozzle for the mouth cavity sanitary device according to the present invention.

The nozzle 37 has a circular circulating hole 37b in the base portion 37a thereof as shown in FIGS. 19 and 20. A C-shaped shutter member 55 is disposed around the base portion 37a. As a result, when the C-shaped shutter member 55 is rotated in a direction designated by an arrow shown in FIG. 20, the degree of opening of the circulating hole 37b can be adjusted. The circulating hole 27b may be formed in an elliptical shape as shown in FIG. 21. The shutter member 55 may, as shown in FIG. 22, be formed in an annular shape having a communication hole 55a.

When the discharge pressure from the nozzle 37 is adjusted, a nozzle 37 having a desired circulating hole 37b is selected so as to be fastened to the nozzle fastening port 12a or the shutter member 55 is rotated so as to adjust the opening degree of the circulating hole 37b in the case where the device comprises the shutter member 55. As a result, the quantity of liquid flowed out through the circulating hole 37b and passing through the circulating passage, that is, the same, flowed out from the nozzle fastening port 12a, passes through the liquid supply port 12b and returns to the reservoir chamber 34, can be adjusted. Therefore, the pressure of liquid to be discharged through the nozzle 37 can be adjusted.

Therefore, according to the present invention, the following effects can be obtained when the pressure of liquid to be discharged through the nozzle is adjusted:

a. Since the pump load is not enlarged, the noise and vibration can be prevented and the durability can be improved.

b. The structure can be formed simply.

c. The number of necessary elements can be reduced.

Figure 23:
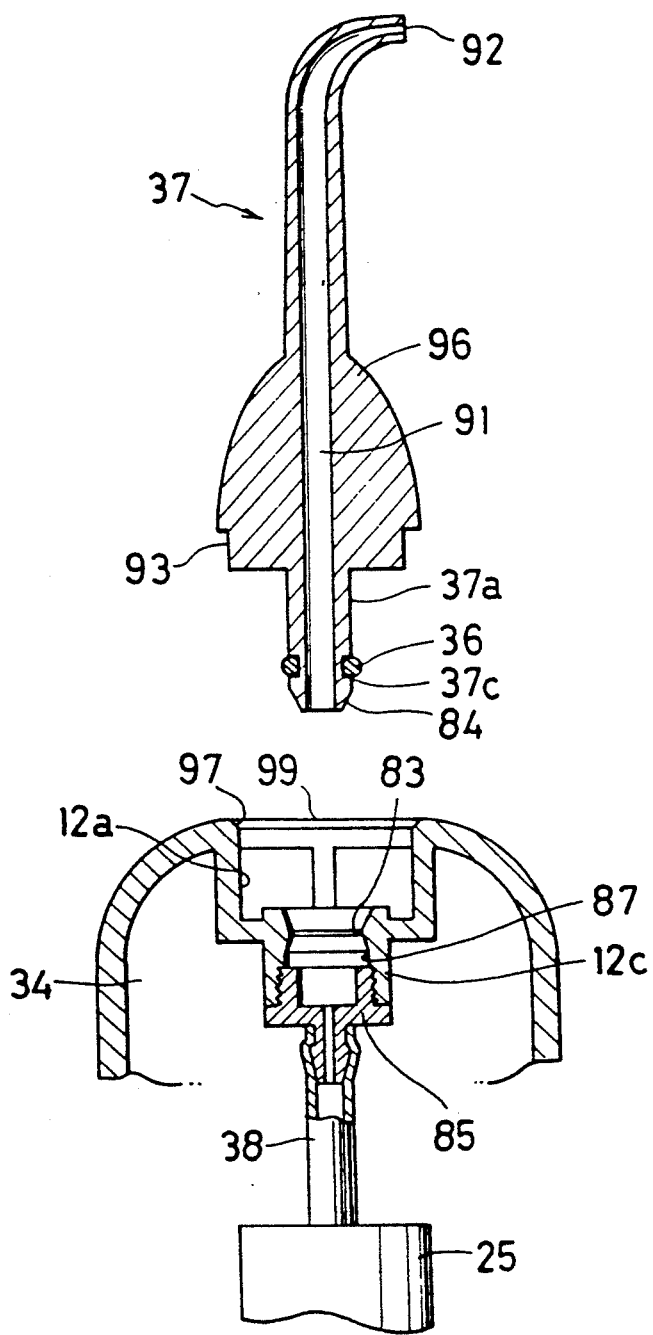
FIG. 23 is a cross sectional view which illustrates the nozzle securing structure of the mouth cavity sanitary device according to the present invention.

FIG. 23 illustrates a structure for securing the nozzle for the mouth cavity sanitary device according to the present invention. A nozzle flange portion 96 is formed close to the base portion 37a of the nozzle 37 including a fluid passage 91. A groove 37c for holding the O-ring 36 is formed on the outer surface of the base portion 37a at a position close to an end portion 84 on the liquid introduction side. When liquid discharged by urging force given by the pump 25 is supplied to the fluid passage 91, liquid can be jetted out through a nozzle discharge port 92. Reference numeral 83 represents a nozzle insertion port into which the end portion 84 of the nozzle 37 is inserted. Reference numeral 87 represents an O-ring fastening portion having a cylindrical or conical inner surface formed next to the nozzle insertion port 83, the O-ring fastening portion 87 being arranged to have the inner diameter which is larger than the inner diameter of the nozzle insertion port 83. On the other hand, the inner diameter of the nozzle insertion port 83 is arranged to be smaller than the outer diameter of the O-ring 36 held by the nozzle 37. The fastening portion 12c for fastening the nozzle 37 has at least the nozzle insertion port 83 and the O-ring fastening portion 87. The connection tube 38 provided for the purpose of introducing liquid discharged by the pump 25 into the fastening portion 12c without leakage is connected to a coupling member 85 arranged to be driven into the fastening portion 12C. The nozzle flange portion 96 disposed close to the base portion 37a can be engaged to an inlet portion 97 of the nozzle fastening port 12c. The inlet portion 97 of the nozzle fastening port 12a acts to control the length of insertion of the nozzle 37. It may be arranged to act to prevent the deviation of the nozzle 37 in the direction perpendicular to the insertion direction of the nozzle 37. According to the embodiment shown in FIG. 23, a stepped portion 93 formed around the lower surface of the nozzle flange portion 96 is arranged to be engaged to the inlet portion 97 of the nozzle fastening port 12a. Furthermore, the nozzle fastening port 12a and the fastening portion 12c are integrally formed with each other and the distance between the inlet portion 97 of the nozzle fastening port 12a, which is engaged with the stepped portion 93 at the time of fastening the nozzle 37, and the O-ring fastening portion 87 is made coincide with the distance between the stepped portion 93 and the O-ring ring 36. Therefore, the outer surface of the O-ring 36 can be brought into close contact with the inner surface connecting the nozzle insertion port 83 and the O-ring fastening portion 87 in a state where the nozzle 37 has been fastened. According to this embodiment, reference numeral 34 represents a reservoir which accumulates liquid so as to supply it to the pump 25. Reference numeral 99 represents an injection port through which liquid is supplied to the reservoir 34. In a state where the nozzle 37 has been inserted, the inlet portion 97 formed around the injection port 99 is engaged to the stepped portion 93 of the nozzle flange portion 96. Therefore, the nozzle flange portion 96 also serves as the cover for the reservoir 34.

Since the inner diameter of the nozzle insertion port 83 is made smaller than the outer diameter of the O-ring 36, the nozzle 37 does not separate even if liquid discharged by the urging force supplied by the pump 25 pushes the nozzle 37 in the direction of the discharge of liquid. Furthermore, since a sealing effect is created by the O-ring 36 and the O-ring fastening portion 87, liquid leakage through the fastening portion 12c can be prevented.

Therefore, according to the present invention, even if the O-ring made of an elastic material such as rubber deteriorates due to the repeated mounting/removing of the nozzle and/or the lapse of time, the O-ring can be easily maintained since the O-ring is held on the outer surface of the nozzle 37.

Furthermore, a necessity of providing a fastening member for preventing the nozzle separation due to the discharge pressure can be eliminated. Therefore, the structure of a nozzle securing means can be simplified.

Figure 24:
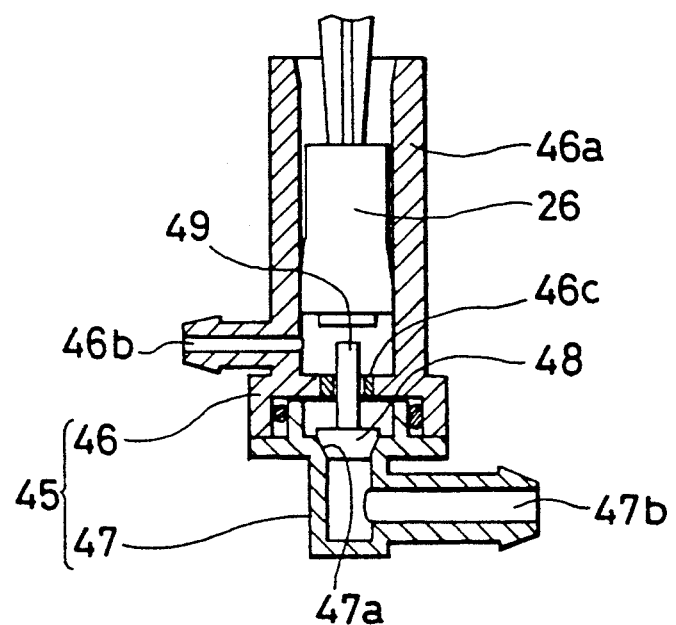
FIG. 24 is a cross sectional view which illustrates the mouth cavity sanitary device according to the present invention.

FIG. 24 is a cross sectional view which illustrates the structure of a pump for the mouth cavity sanitary device according to the present invention. The pump 25 shown in FIG. 6 is constituted as shown in FIG. 24. That is, a pump case 45 is constituted by a first and a second pump cases 46 and 47. The first pump case 46 is provided with a cylinder 46a, a discharge port 46b and a valve supporting portion 46c. Furthermore, the piston 26 is, as shown in FIG. 24, accommodated in the cylinder 46a in such a manner that the piston 26 can perform the reciprocating motion. The discharge portion 46b is formed so as to project to the left when viewed in the drawing. The valve supporting portion 46 supports a stop valve 48 in such a manner that its operation direction is the same (in the vertical direction when viewed in the drawing) as that of the piston 26 and the stop valve 48 can perform the reciprocating motion. Furthermore, the second pump case 47 is hermetically connected to the lower portion of the first pump case 46. The second pump case 47 is provided with a valve seat 47a and a suction port 47b. The stopper valve 48 is arranged to abut against the valve seat 47a. The suction port 47b is disposed lower than the discharge port 46 and is arranged to project to the right when viewed in the drawing. As a result, the piston 26 can be reciprocated with the stopper valve 48 opened/closed so that liquid sucked through the suction port 47b into the cylinder 46a is discharged through the discharge port 46b. If the stop valve 48 is not returned to the close position due to the compression operation of the piston 26, a valve rod 49 is pushed by the front portion of the piston 26 so that the stop valve 48 is pushed toward the valve seat 47a.

Therefore, according to the pump thus constituted, since the discharge port is positioned higher than the suction port, air introduced into the pump case cannot be accumulated in the cylinder, but it is discharged through the discharge port. As a result, the non-uniform discharge pressure or the reduction in the discharge pressure can be prevented.

Furthermore, a necessity of providing the conventional valve supporting member or a third pump case can be eliminated. Therefore, the number of the necessary elements can be reduced.

In addition, even if the smooth reciprocating motion of the stop valve is hindered due to a viscous material contained in liquid and the stop valve is not thereby returned to the close position due to the compression operation of the piston, the valve rod is pushed by the piston and the stop valve is thereby pushed toward the valve seat. Therefore, a desired pump function can be secured and the reduction in the discharge pressure of liquid can be prevented.

Figure 25:
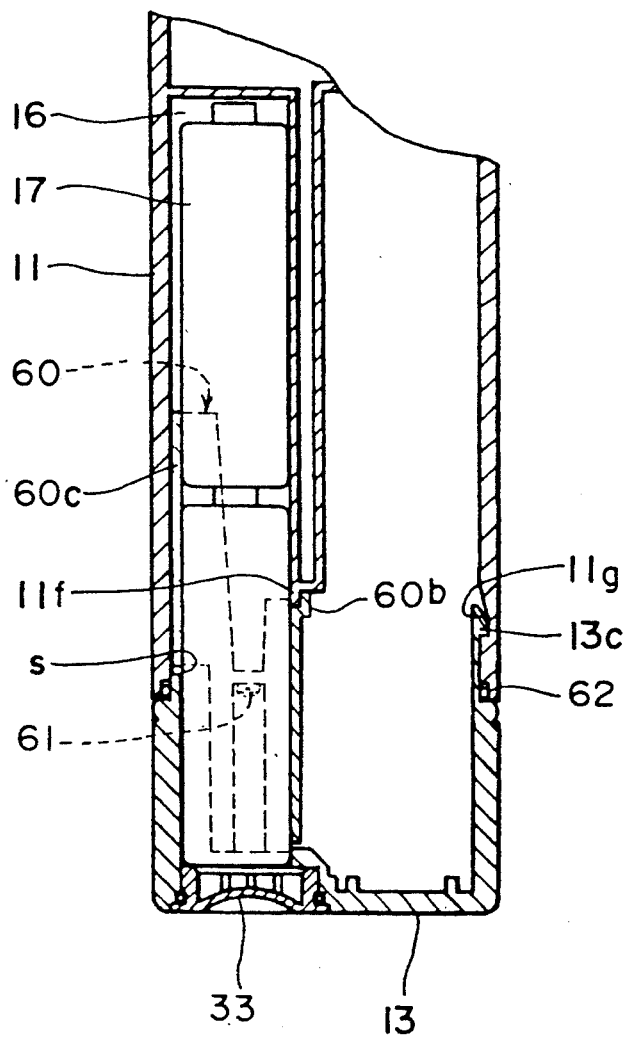
FIG. 25 is a partial cross sectional view which illustrates a structure for fastening a lower case to the body case of the mouth cavity sanitary device according to the present invention.

FIG. 25 is a partial cross sectional view which illustrates a structure for fastening the lower case to the body case for a mouth cavity sanitary device according to the present invention.

Figure 26:
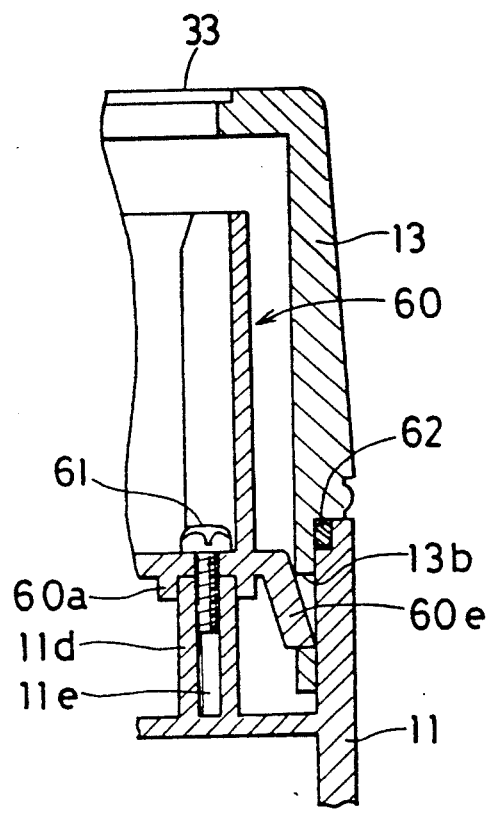
FIG. 26 is a partial cross sectional view which illustrates an inverted state of the structure for fastening a lower case to the body case of the mouth cavity sanitary device according to the present invention.

FIG. 26 is an inverted partial cross sectional view which illustrates the structure for fastening the lower case to the body case shown in FIG. 25.

Hitherto, the conventional mouth cavity sanitary device has been arranged in such a manner that an opening formed in the body case is covered by a cap after each of the elements has been fastened. Then, the cap is, for example, adhered, with an adhesive, to the body case or the same is ultrasonic-welded to the body case on which a small projection is formed. Furthermore, a packing 4 is compressed between the above-described two elements and the male-fastening portion is fastened to the female fastening portion.

However, if an adhesive is used, there arises a fear of contamination of the appearance by the overflowed adhesive. Therefore, the fastening of the cap necessitates a complicated labor. Furthermore, cap has not been able to be removed and the reliability of the waterproofing has been thereby unsatisfactory. Although the fear of contaminating the appearance can be eliminated if the ultrasonic-welding is employed, a special welding facility becomes necessary. Furthermore, the removal of the cap has been also impossible and the reliability of the waterproofing has been unsatisfactory. In the case where the packing is used, the fear of contaminating the appearance can be eliminated and satisfactory reliability of waterproofing can be obtained. However, the cap cannot be removed and the structure of the mold becomes too complicated. Therefore, a problem arises in that the size of the case cannot be reduced.

According to the present invention, as shown in FIG. 26, a battery-guide fastening portion 11d is downward (upwards when viewed in FIG. 26) formed in the body case 11, the battery-guide fastening portion 11d having two thread holes 11e. A portion 60a is fitted to the front end portion of the battery-guide fastening portion 11d and another portion 60b is fitted to a positioning portion 11f as shown in FIG. 25. Then, two screws 61 are driven into the two thread holes 11e so that the battery guide 60 is screw-fixed into the body case 11.

Figure 27:
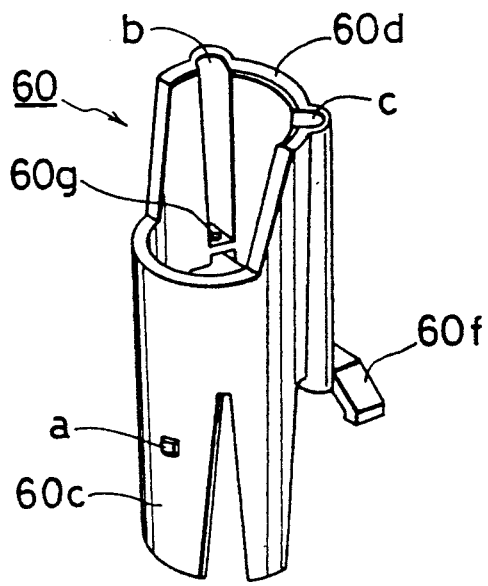
FIG. 27 is a perspective view which illustrates the battery guide shown in FIG. 26.
Figure 28:
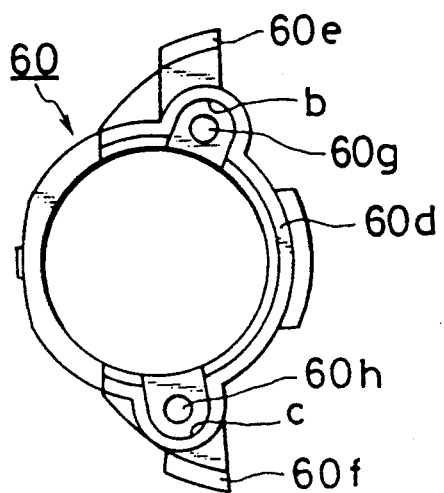
FIG. 28 is a bottom view of the same.
Figure 29:
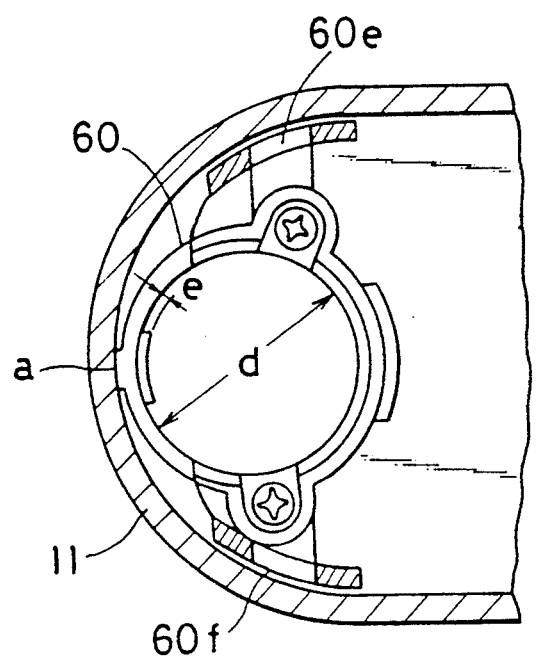
FIG. 29 is a bottom view which illustrates a state where the battery guide is assembled to the body case.

The battery guide 60 is arranged, as shown in FIGS. 27 and 28, that semi-cylindrical battery guide portions 60c and 60d are alternately elongated upwards and downwards. Fastening portions 60e and 60f projecting laterally are formed in the intermediate portion of the battery guide portions 60c and 60d. Furthermore, through holes 60g and 60h through which the screws 51 are respectively inserted are formed in the battery guide portions 60c and 60d. A projection a is formed on the outer surface of the upper batter-guide portion 60c, while small semi-cylindrical relief portions b and c for preventing the contact with the screw 51 are formed in the lower battery guide portion 60d. When, the battery guide 60 is screw-fixed in the body case 11, the projection a is, as shown in FIG. 29, brought into contact with the body case 11. As a result, the projection a is deformed and its diameter d is compressed by e.

Figure 30:
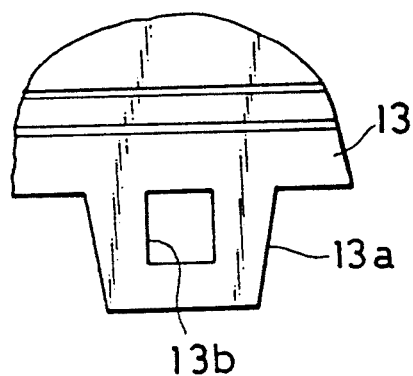
FIG. 30 is a partial enlarged view which illustrates the lower case for the mouth cavity sanitary device according to the present invention.

As shown in FIGS. 25 and 26, the lower case 13 is fitted to the body case 11 with compressing the packing 62 in association with the body case 11 so that the opening in the body case 11 is covered. Two upward projections 13a shown in FIG. 30 are formed on the lower case 13 and a fastening portion 13b is formed in each of the two projections 13a. Thus, when the lower case 13 is fitted to the body case 11, the fastening portions 60e and 60f are fastened to the fastening portions 13b as shown in FIGS. 26 and 29 with the opening covered. According to this embodiment, a fastening portion 13c of the lower case 13 is fastened to a fastening portion 11g of the body case 11.

As shown in FIGS. 25 and 26, the lower case 13 has a battery cover 33. The batteries 17 are positioned in the battery accommodating portion 16 with an assistance of the battery guide 60 after the battery cover 33 has been removed. Then, the battery cover 33 is again fastened. The batteries 17 accommodated in the battery accommodating portion 16 are pressed by the portion, which has been compressed by e, of the battery guide 60. Therefore, even if the diameter of the battery deviates from the standard by a certain degree, the looseness of the batteries can be prevented.

When the batteries 17 are desired to be exchanged, the battery cover 33 is removed so as to remove the batteries 17. Then, new batteries 17 are placed before fastening the battery cover 33.

As shown in FIG. 25, a stepped portion s is formed in the inner surface of the outer case 10 at a position between the body case 11 and the lower case 12. However, according to this embodiment, the upper battery-guide portion 60c can be introduced into the stepped portion s so that the stepped portion s can be eliminated. Furthermore, the upper battery-guide portion 60c extends to the side surface of the battery 17 which has been previously placed. Therefore, the batteries 17 can be smoothly placed by the battery guide 60.

When the lower case 13 is removed, the battery cover 33 is removed and the screw 61 is also removed by, for example, a screw driver so as to release the screw fixing. When the lower case 13 is, by a certain degree, shifted, the fastening state between the fastening portions 13c and 11g can be cancelled so that the lower case 13 can be, together with the battery guide 60, removed.

Therefore, according to the present invention, the following effects can be obtained:

(1) The fear of overflowing of the adhesive agent at the time of the assembling work can be eliminated and a necessity of providing a special facility can be eliminated. Furthermore, the assembling of the elements can be completed only by the insertion operation without the necessity of the adhesion and the welding. Therefore, the fastening of the lower case can be easily completed.

(2) The lower case can be removed and the repair work can thereby be performed easily.

(3) Since the cap is fastened with compressing the packing in association with the body case, the reliability of waterproofing can be improved.

(4) The structure of the molding can be simplified and the size of it can be reduced.

(5) The batteries can be easily changed by the action of the battery guide.

The portable mouth cavity sanitary device is arranged in such a manner that the switch button thereof is depressed so as to operate the motor provided therein. The structure of the switch of the type described above is arranged in such a manner that the switch button is urged outwards by using a return spring. When motor is operated, the switch button is depressed against the urging force of the return spring. Thus, the contacts are brought into contact with each other so that the motor is operated. However, the following problems arise in this case:

(1) The length of the return spring must be elongated in order to stabilize the urging force. Therefore, a large space is necessary in the lengthwise direction.

(2) Since the switch button must be independently handled from the return spring, the efficiency in the assembling work deteriorates.

Figure 31:
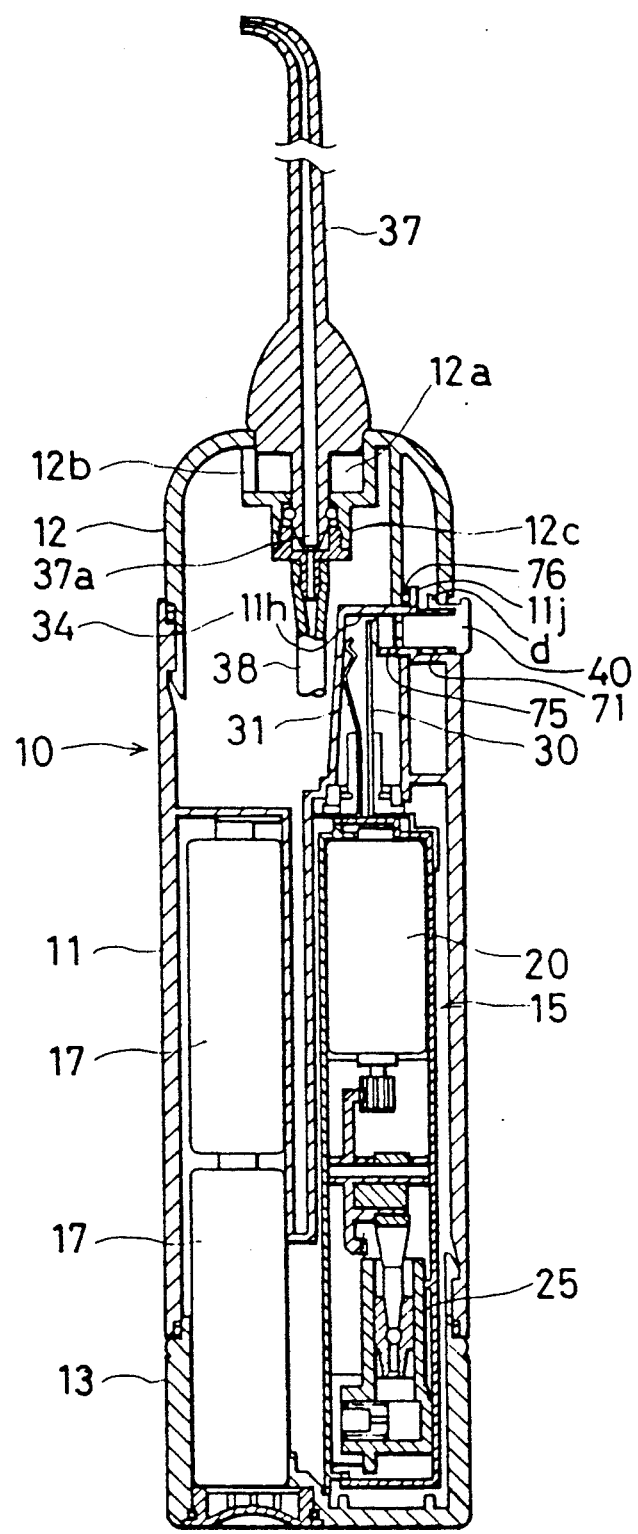
FIG. 31 is an overall vertical cross sectional view which illustrates the mouth cavity sanitary device having a switch structure according to the present invention.
Figure 32:
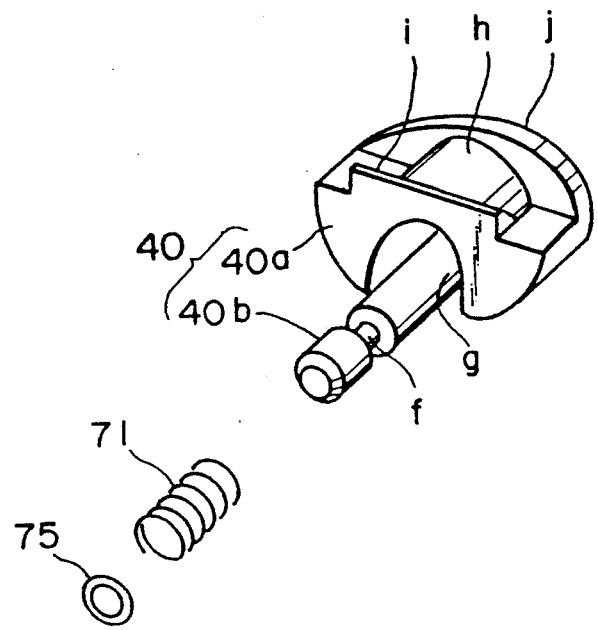
FIG. 32 is an exploded perspective view which illustrates the switch button portion shown in FIG. 31.

In the mouth cavity sanitary device according to the present invention, the switch button 40 is fastened to the upper portion of the body case 11 as shown in FIG. 31. The switch button 40 comprises, as shown in FIG. 32, the head portion 40a and a cylindrical portion 40b which has a circumferential groove f at the front end portion thereof. The head portion 40a has a semicircular groove g along the outer surface of the cylindrical portion 40b and has, in the upper portion thereof, a straight fastening groove h which is not communicated with the semicircular groove g. Furthermore, an abutting portion i and a fastening portion j are disposed so as to run parallel with each other with the fastening groove h held therebetween. A coil spring 71 is fitted within the semicircular groove g and around the outer surface of the cylindrical portion 40b, while an O-ring 75 is fitted within the circumferential groove f. As shown in FIG. 31, the front end portion of the cylindrical portion 40b is fitted within a lateral hole 11h formed in the body case 11 with compressing the O-ring 75. Furthermore, an end portion of the coil spring 71 is abutted against an inlet portion 11j of the lateral hole 11h so as to outwards urge the switch button 40, the switch button 40 being then fastened to the body case 11 in such a manner that the switch button 40 can be slid. The upper case 12 is fastened to the body case 11 with compressing a packing 76 in association with the body case 11. Thus, the abutting portion i of the switch button 40 is abutted against the inner surface of the upper case 12 by the urging force of the coil spring 71 so that the separation of the switch button 40 is prevented. As a result, the switch button 40 is disposed in such a manner that its front end portion confronts the front end portion of the switch spring 30 and is outwards urged by the coil spring 71 with its head portion 40a projected outwards. When, the switch button 40 is depressed against the coil spring 71, the two switch springs 30 and 31 are brought into contact with each other so that the motor 20 is operated.

When the thus constituted mouth cavity sanitary device is used, water or chemical (for example, mouth cavity cleaning liquid or liquid obtained by diluting it) is introduced through the nozzle fastening port 12a of the upper case 12 and the liquid supply port 12b into the reservoir chamber 34. After the reservoir chamber 34 has been filled with liquid thus introduced, the base portion 37a is fitted to the fastening portion 12c before capping the nozzle fastening port 12a with the nozzle 37. Then, the outer case 10 is held by a user who has become slouchy and the nozzle 37 is directed at the mouth cavity before depressing the switch button 40. When the hand is released from the switch button 40, the switch button 40 can be automatically returned by an action of the return spring 71. As a result, the contact between the two switch springs 30 and 31 is released so as to stop the rotation of the motor 20. Therefore, the operation of the pump 25 is stopped and the jetting out of liquid through the nozzle 37 is stopped.

Figure 33:
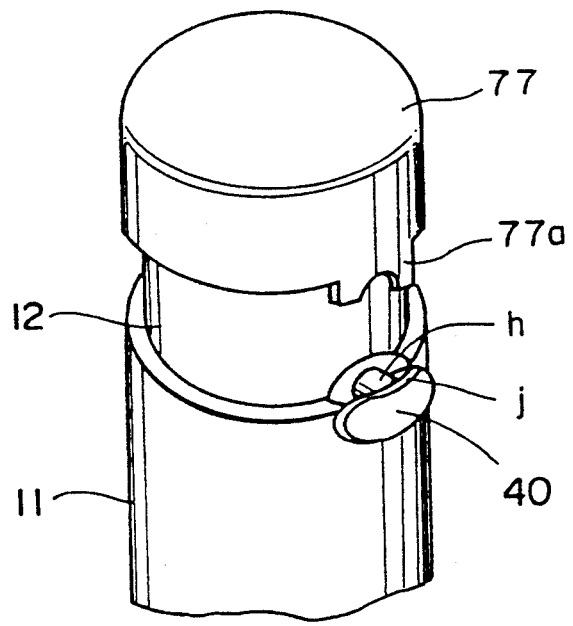
FIG. 33 is a perspective view which illustrates the mouth cavity sanitary device having a switch structure according to the present invention in a state where the outer cap is being fastened to the outer case.

When the use of the mouth cavity sanitary device is ended, the nozzle 37 is removed and an outer cap 77 is fastened to the upper case 12 as shown in FIG. 33. The outer cap 77 has a fastening projection 77a formed thereon, the fastening projection 77a being fitted within the fastening grove h formed in the switch button 40 at a position between the upper case 12 and the fastening portion j. As a result, the operation of the switch button 40 by depressing it can be made impossible. Therefore, undesirably pushing operation of the switch button 40 can be prevented during the transportation of the device.

According to this embodiment, since the switch button 40 is arranged in such a manner that the semicircular groove g and the fastening groove h are not communicated with each other, the coil spring 71 can be covered, causing an excellent appearance to be obtained.

Therefore, according to the thus arranged structure, the following effects can be obtained:

(1) Since the coil spring is employed as the return spring for use in the switch button, the necessary area can be reduced, causing the overall size of the portable mouth cavity sanitary device to be reduced.

(2) Since the coil spring the cost of which is lower than that of the return spring is used, the overall cost can be reduced.

(3) Since the coil spring can be fastened to the switch button and the above-described two elements can be integrally handled, the assembling work can be easily performed.

Figure 34:
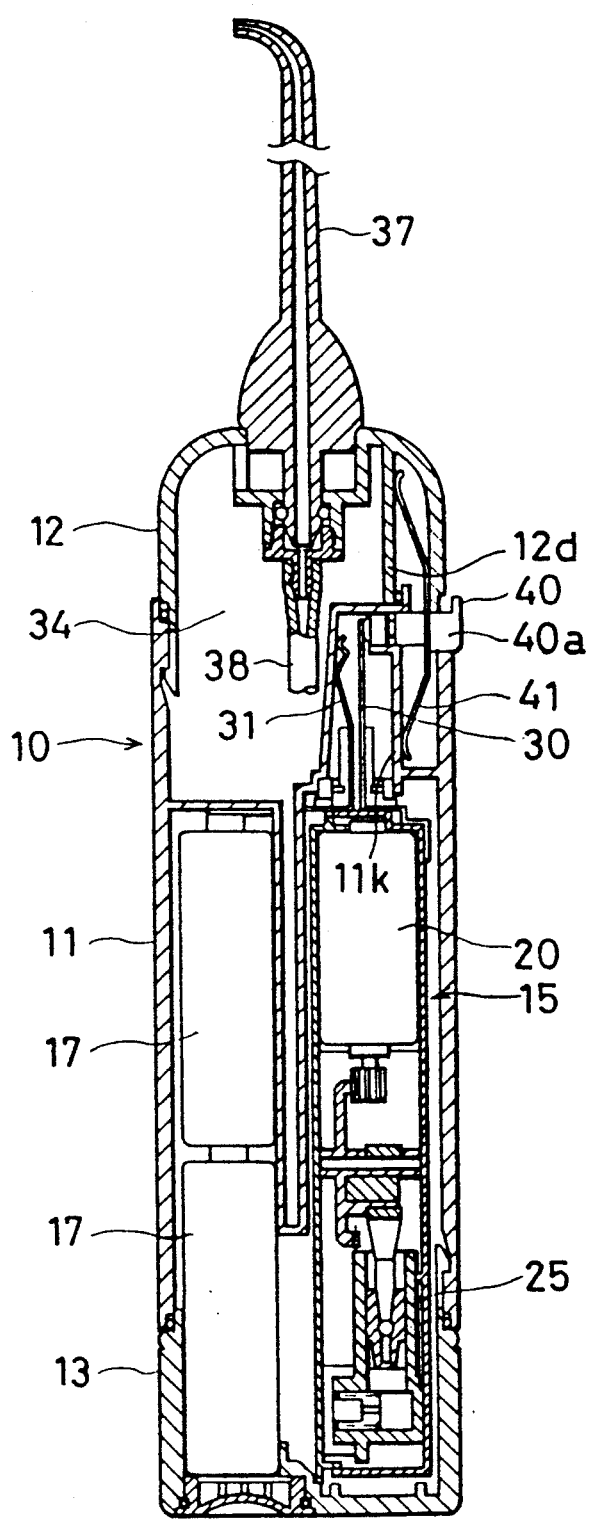
FIG. 34 is an overall vertical cross sectional view which illustrates the mouth cavity sanitary device having a switch structure according to an embodiment of the present invention.

The structure of the switch for the mouth cavity sanitary device according to the present invention is constituted as follows in order to reduce the necessary number of the switch elements, improve the assembling facility, reduce the necessary space, and thereby reduce the overall size of the device:

FIG. 34 illustrates the mouth cavity sanitary device having a switch structure according to an embodiment of the present invention.

Figure 35:
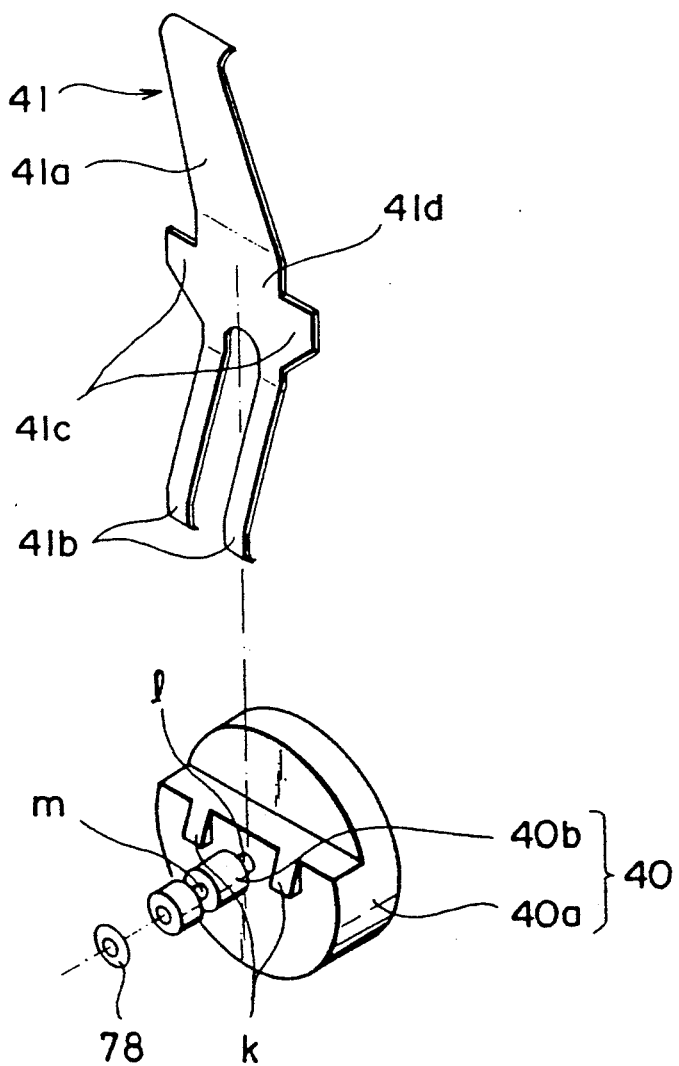
FIG. 35 is a perspective view which illustrates a return spring, a switch button and a packing.

As shown in FIG. 34, the switch button 40 is fastened to the upper portion of the body case 11. As shown in FIG. 35, the switch button 40 comprises the head portion 40a in the form of a button and the cylindrical portion 40b straight extending from the inner surface of the head portion 40a. The head portion 40a has fastening projections k on the inner surface thereof, while the cylindrical portion 40b has a fastening groove l at the root portion thereof and has a packing groove m close to the front end portion thereof. Then, a packing 78 is fitted within the packing groove m as shown in FIG. 35, while the front end portion of the cylindrical portion 40b is, as shown in FIG. 34, fastened to the outer case 10 so as to confront the front end portion of either of the switch springs 30 in such a manner that the cylindrical portion 40b can be slid. Furthermore, the return spring 41 is fitted within the fastening groove 1. As shown in FIG. 35, the return spring 41 comprises a body 41a, leg portions 41b branched into two sections and fastening arm portions 41c laterally extending at an intermediate position between the body 41a and the leg portions 41b. The return spring 41 is fastened from an upper portion so as to fit a branch portion 41d into the fastening groove 1. Furthermore, the two fastening arm portions 41c are fastened to the fastening projections k so that the return spring 41 is fastened so as not to be separated from the switch button 40. Then, the upper case 12 is fastened to the body case 11 and the front end portions of the two leg portions 41b are, as shown in FIG. 34, abutted against a wall portion 11a of the body case 11. Furthermore, the front end portion of the body portion 41a is abutted against a wall portion 12d of the upper case 12. As a result, the portion in the vicinity of the branch portion 41d of the return spring 41 is abutted against the inner surface of the upper case. As a result, the separation of the switch button 40 can be prevented and the head portion 40a of the switch button 40 is projected over the outer case 10 by the urging force of the return spring 41. Thus, when the switch button 40 is depressed against the urging force of the return spring 41, the two switch springs 30 and 31 are brought into contact with each other so that the motor 20 is operated.

Therefore, as a result of the thus constituted switch structure, the following effects can be obtained:

(1) Since the separation of the switch button is prevented by the return spring, a necessity of providing an independent separation stopper such as an E-ring can be eliminated. Therefore, the number of the necessary elements can be reduced.

(2) Since the necessity of the provision of the E-ring which is difficult to be fastened in a portable mouth cavity sanitary device can be eliminated, the assembling facility can be improved.

(3) Since a return spring is employed in the switch button, the necessary space can be reduced with respect to a case in which a coil spring is employed. Therefore, an advantage can be obtained in that a portable mouth cavity sanitary device is realized.

Figure 36A:
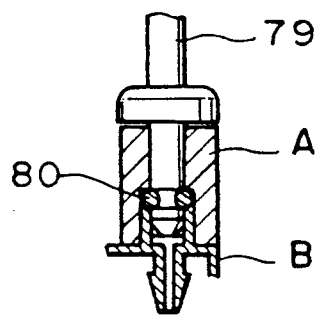
FIGS. 36(a) to 36(c) are cross sectional views which illustrate the structure of the nozzle fastening portion according to an embodiment of the present invention.
Figure 36B:
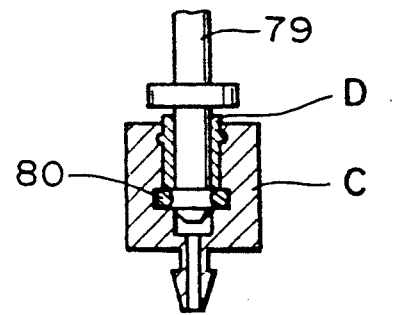
Figure 36C:
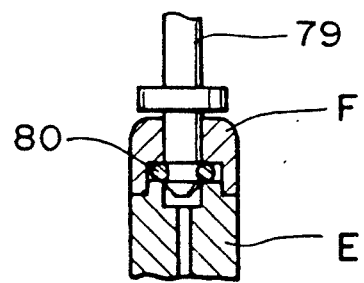

As shown in FIGS. 36(a) to 36(c), the nozzle for the mouth cavity sanitary device can be arranged detachable.

For example, a nozzle 79 is arranged detachable as a result of the structure constituted as shown in FIG. 36(a) and 36(c). For example, as shown in FIG. 36(a), a member B is driven into a member A, while a member D is forcibly inserted into a member C as shown in FIG. 36(b). A member F is welded to a member E as shown in FIG. 36(c). As a result, the packing 80 is held in each of the above-described structures. Thus, the space between the nozzle 79 and the nozzle fastening portion is hermetically sealed by the packing 80 after the nozzle 79 has been fastened. However, the driving structure as shown in FIG. 36(a) shows a problem in that the assembling facility is unsatisfactory. According to the forcible insertion method as shown in FIG. 36(b), a problem arises in that the element decomposition cannot be performed. Also according to the welding method as shown in FIG. 36(c), the elements decomposition cannot be performed and what is even worse a welding facility is necessary to be provided.

Then, a structure exhibiting an excellent assembling facility of the nozzle fastening portion of the mouth cavity sanitary device, capable of being decomposed, and easily manufactured without a necessity of a special facility will be described with reference to the drawings.

Figure 37:
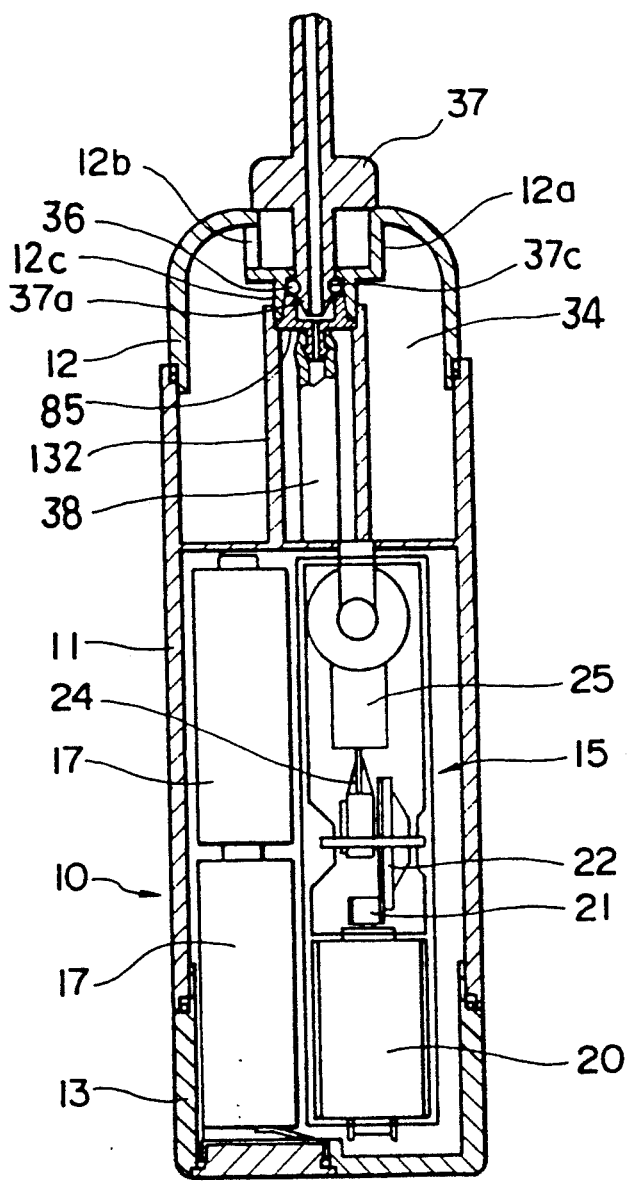
FIG. 37 is a vertical cross sectional view which illustrates the mouth cavity sanitary device having the nozzle fastening portion according to the present invention.

FIG. 37 illustrates a portable mouth cavity sanitary device having an improved nozzle fastening portion. Since the elements of the structure according to the embodiment shown in FIG. 6 are similar to this embodiment, the descriptions for the elements are omitted here.

The outer case 10 has the reservoir chamber 34 in the upper portion thereof. Although omitted from the illustration, the reservoir chamber 34 is connected to the suction side of the pump 25. A cylindrical post 132 is erected in the reservoir chamber 34. A coupling member 85 is placed on the top end portion of the cylindrical post 132. An end portion of the connection tube 38 is fastened to the coupling member 85. Another end portion of the connection tube 38 is connected to the discharge side of the pump 25. A recessed portion is formed in the top end portion of the outer case 10, that is, the top end portion of the upper case 12. The nozzle fastening port 12a is formed so as to face downwards. When the upper case 12 is fastened to the body case 11, the fastening portion 12c formed next to the nozzle fastening port 12a is fitted to the coupling member 85 so that the O-ring 36 is held therebetween. Then, the base portion 37a is fitted to the fastening portion 12c and the nozzle 37 is detachably fastened. As a result, the O-ring 36 is fitted within the packing groove 37c of the nozzle 37 so that the space between the nozzle 37 and the fastening portion 12c is hermetically sealed. Therefore, the liquid leakage from the gap between the base portion 37a and the fastening portion 12c can be prevented by the O-ring 36.

When the thus constituted mouth cavity sanitary device is used, water or chemical (for example, mouth cavity cleaning liquid or liquid obtained by diluting it) is introduced through the fastening portion 12c of the upper case 12 and the liquid supply port 12b into the reservoir chamber 34. After the reservoir chamber 34 has been filled with liquid thus introduced, the base portion 37a is fitted to the fastening portion 12c before capping the recessed portion with the nozzle 37. Then, the outer case 10 is held by a user who has become slouchy and the nozzle 37 is directed at the mouth cavity before depressing the switch button (omitted from illustration). As a result, the motor 20 is operated so that the motor gear 21 is rotated, causing the crown gear 22 to be rotated. Therefore, the piston is reciprocated via the crank 24 so that the stop valve is opened against the urging force of the urging spring in the suction stroke, causing liquid enclosed in the reservoir chamber 34 to be introduced. In the discharge stroke, the stop valve is closed so as to upwards send the thus introduced liquid. Then, liquid is jetted out through the nozzle 37 so as to be discharged in the mouth cavity. As a result, the mouth cavity can be cleaned up and the mouth cavity can be refreshed. When the hand is released from the switch button, the rotation of the motor 20 is stopped. Therefore, the operation of the pump 25 is stopped and the jetting out of liquid through the nozzle 37 is stopped.

Figure 38:
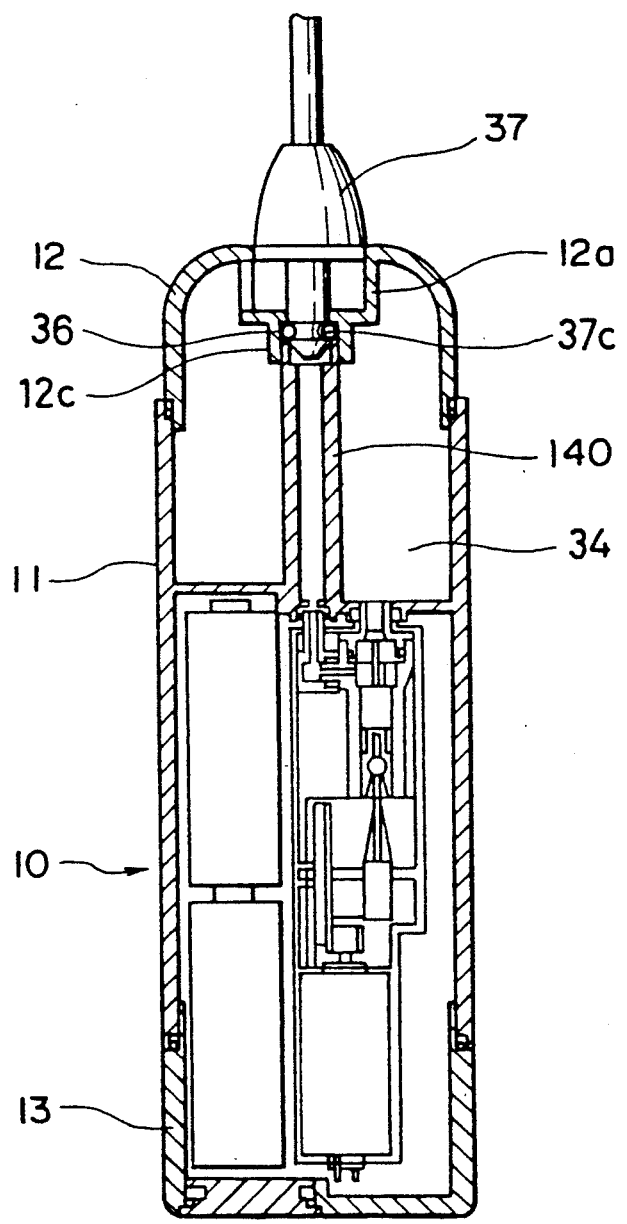
FIG. 38 is a vertical cross sectional view which illustrates another embodiment of the mouth cavity sanitary device having the nozzle fastening portion according to the present invention.

According to the above-described embodiment, the coupling member 85 is placed on the cylindrical post 132 disposed in the reservoir chamber 34 and the O-ring 36 is held via the coupling member 85. However, another structure as shown in FIG. 38 may be employed in which the O-ring 36 is directly held by a cylindrical post 140 disposed in the reservoir chamber 34.

Therefore, according to the thus constituted structure, the packing can be held by a simple fitting with eliminating the conventional necessity of performing the driving fixing, forcible insertion or welding. Therefore, the nozzle fastening portion can be easily formed by a manner in which the assembling work can be performed easily, the element decomposition can be performed and a special facility is not necessary.

Although the invention has been described in its preferred form with a certain degree of particularly, it is understood that the present disclosure of the preferred from has been changed in the details of construction and the combination and arrangement of parts may be resorted to without departing from the spirit and the scope of the invention as hereinafter claimed.

What is claimed is:

1. A mouth cavity sanitary device for discharging liquid through a nozzle by urging and sucking liquid in a reservoir chamber by operating a pump, said mouth cavity sanitary device comprising:
   a fastening portion formed in an outer case for receiving an end portion of said nozzle;
   a circulating hole formed in said nozzle;
   a circulating passage formed in the fastening portion of said nozzle, said circulating passage acting to return a part of liquid flowed out through said circulating hole to said reservoir chamber; and
   a means for adjusting a degree of opening of said circulating hole whereby the discharge pressure of the liquid may be adjusted.

2. A liquid urging device according to claim 1, wherein said means for adjusting a degree of opening comprises a shutter member for adjusting the opening degree of said circulating hole fastened to said nozzle.

3. A mouth cavity sanitary device comprising:
   a nozzle including a liquid passage formed therein and including a nozzle flange portion which has an outer groove formed at an end portion of said nozzle to which an O-ring is fitted within said outer groove;
   an outer case to which said nozzle is fitted;
   a nozzle fastening port formed in said outer case and having an inlet portion which can be engaged with said nozzle flange portion when said nozzle is fastened to said outer case;
   a fastening portion for receiving said end portion of said nozzle through said nozzle fastening portion, said fastening portion comprising a nozzle insertion port whose inner diameter is smaller than the outer diameter of said O-ring, an O-ring fastening portion, the inner diameter of which is larger than the inner diameter of said nozzle insertion port and a tapered portion between said O-ring fastening portion and said nozzle insertion port.

* * * * *